United States Patent [19]

Oppenhein et al.

[11] Patent Number: 5,126,252
[45] Date of Patent: Jun. 30, 1992

[54] EXPRESSIONS VECTORS CONTAINING LAMBDA PL PROMOTER AND $T_1 T_2$ RNA TERMINATION SEQUENCE, PLASMIDS CONTAINING THE VECTORS, HOSTS CONTAINING THE PLASMIDS AND RELATED METHODS

[75] Inventors: Amos B. Oppenheim, Jerusalem; Avigdor Levanon, Netanya; Hilla Locker-Galadi, Jerusalem; Marian Gorecki, Rehovot, all of Israel

[73] Assignee: Bio-Technology General Corp., New York, N.Y.

[21] Appl. No.: 317,434

[22] Filed: Mar. 1, 1989

Related U.S. Application Data

[63] Continuation of Ser. No. 644,671, Aug. 27, 1984, abandoned.

[51] Int. Cl.$^5$ ............... C12N 15/18; C12N 15/63; C12N 15/70; C12N 15/73
[52] U.S. Cl. ............... 435/69.4; 435/252.33; 935/38; 935/29; 935/60; 935/72
[58] Field of Search ............... 435/320, 69.1, 172.3, 435/252, 33; 935/41, 42, 43, 45, 60, 73, 320.1, 69.4

[56] References Cited

U.S. PATENT DOCUMENTS

| | | | |
|---|---|---|---|
| 4,559,300 | 12/1985 | Kovacevic et al. | 435/69.1 |
| 4,578,355 | 3/1986 | Rosenberg | 435/317 |
| 4,710,473 | 12/1987 | Morris | 435/320.1 |

FOREIGN PATENT DOCUMENTS 0041767 12/1981 European Pat. Off.

OTHER PUBLICATIONS

Warburton et al., Nucleic Acids Research vol 11, No. 17, pp. 5837-5854 (1983).
Brosius, J., Gene 27: 161-172 (1984).
Stueber, D. et al., The EMBO Journal vol. 1, No. 11, pp. 1399-1404 (1982).
Lautenberger et al, Science 221, pp. 858-860 (1983).
Shatzman et al, 14th Miami Winter Symposium, p. 98 (1982).
Amann et al, Gene 25, pp. 167-178 (1983).
Zabeau et al, EMBO, vol. 10, pp. 1217-1224 (1982).
Hedgpeth et al, MGG 163, pp. 197-203 (1978).
Bernard et al, Gene 5, pp. 59-76, (1979).
Derom et al, Gene 17, pp. 45-54 (1982).
Gheysene t al, Gene 17, pp. 55-63 (1982).
Remaut et al, Gene 22, pp. 103-113 (1983).
Derynck et al, Nature 287, pp. 193-197 (1980).
Oppenheim et al, JMB 158, pp. 327-346 (1982).
Shimatake et al, Nature 292, pp. 128-132 (1981).
Courtney et al, PNAS, 81, pp. 669-673, (1984).
Lauteberger et al Gene 23, pp. 75-84 (1983).
Seeburg et al; DNA, vol. 2, #1, pp. 37-45 (1983).
Brosius et al.; J. Mol. Biol. (1981) 148, pp. 107-127.

*Primary Examiner*—Richard A. Schwartz
*Assistant Examiner*—S. L. Nolan
*Attorney, Agent, or Firm*—John P. White

[57] ABSTRACT

An improved vector upon introduction into a suitable host containing the thermolabile repressor $C_I$ renders the host capable of effecting expression of a desired gene. The vector is a double-stranded DNA molecule which includes in 5' to 3' order the following: the promoter and operator $P_L O_L$ from lambda bacteriophage; the N utilization site; a first restriction enzyme site permitting replacement of the ribosomal binding site which follows thereafter; a ribosomal binding site; an ATG initiation codon or DNA which is converted into an ATG initiation codon upon insertion of the desired gene into the vector; a second restriction enzyme site for inserting the gene in phase with the ATG codon; a $T_1 T_2$ rRNA transcription termination sequence; an origin of replication and a gene associated with a selectable or identifiable phenotypic trait manifested when the vector is present in the host. The distance between the 3' end of the $P_L O_L$ promoter and operator sequence and the 5' end of the N utilization site is less than about 80 base pairs and the distance between the 3' end of the N utilization site and the 5' end of the ribosomal binding site is less than about 300 base pairs.

Plasmids have been constructed from the vectors and used to produce bovine, chicken and porcine growth hormones, human apolipoprotein E and human superoxide dismutase.

9 Claims, 24 Drawing Sheets

Figure 19
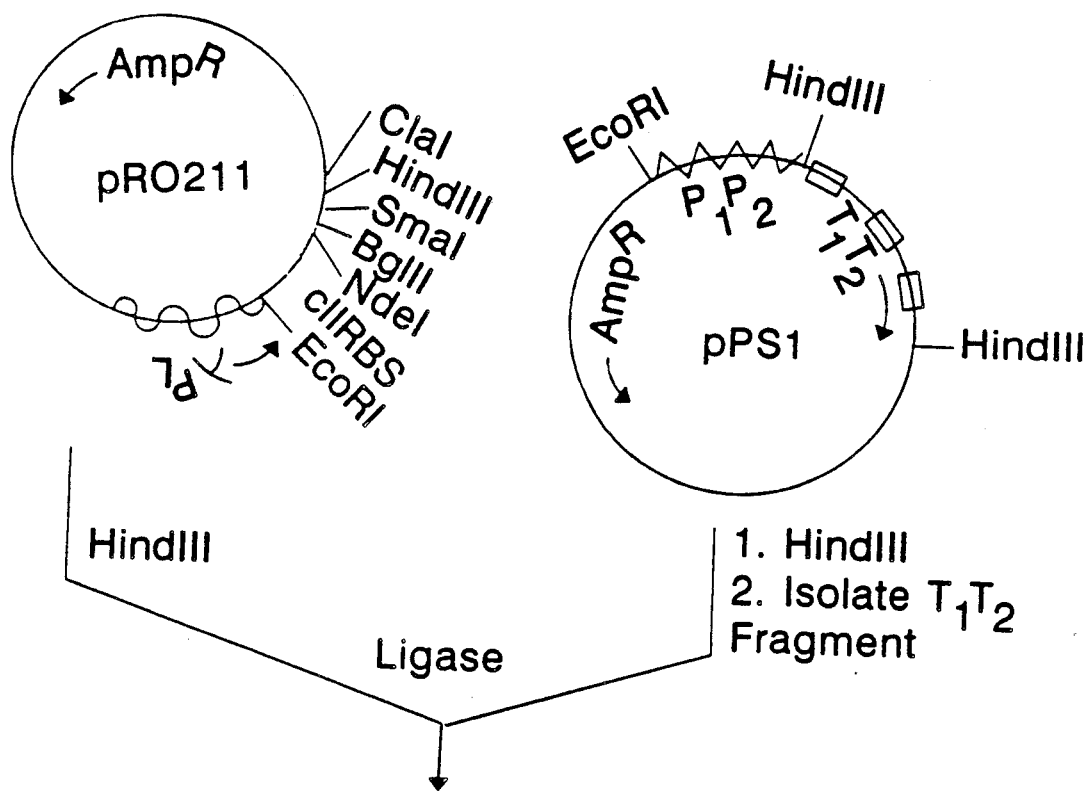
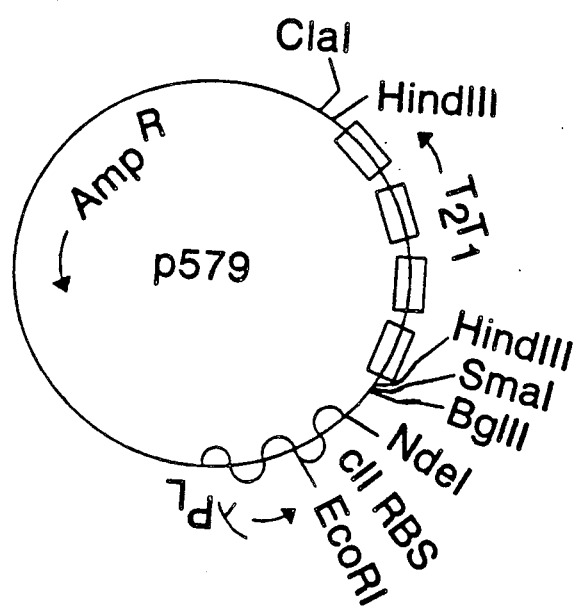

Figure 21
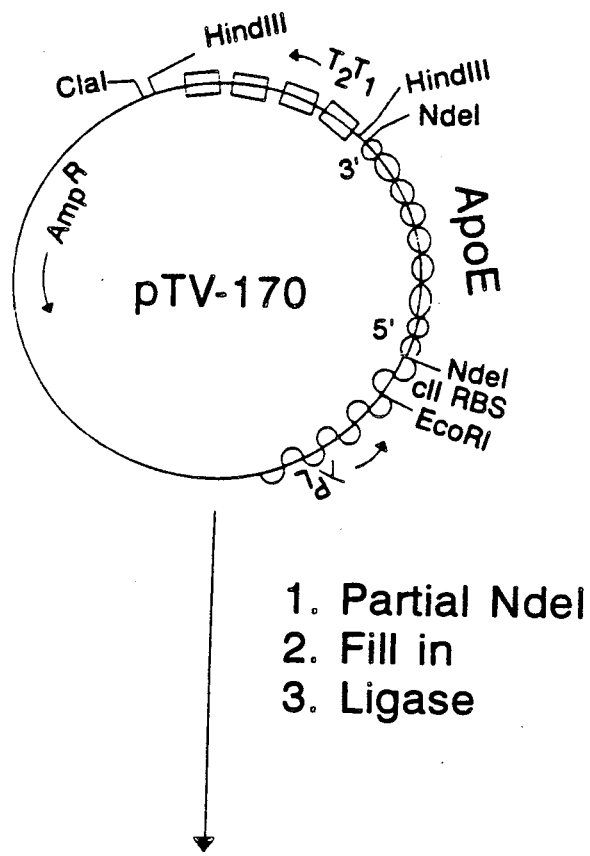
1. Partial NdeI
2. Fill in
3. Ligase
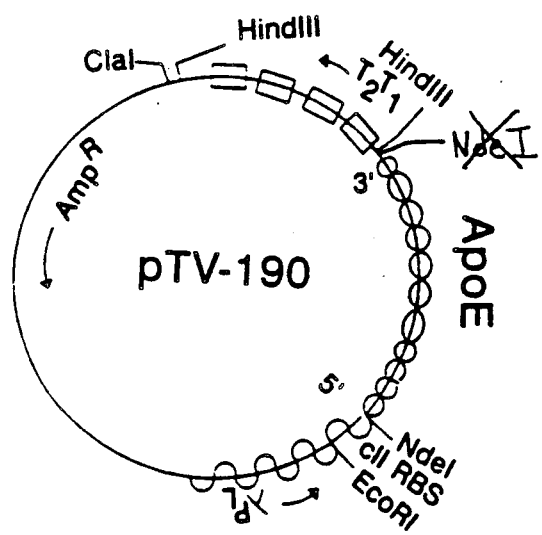

EXPRESSIONS VECTORS CONTAINING LAMBDA PL PROMOTER AND $T_1$ $T_2$ RNA TERMINATION SEQUENCE, PLASMIDS CONTAINING THE VECTORS, HOSTS CONTAINING THE PLASMIDS AND RELATED METHODS

This application is a continuation of U.S. Ser. No. 644,671, filed Aug. 27, 1984, now abandoned, the contents of which are hereby incorporated by reference.

BACKGROUND OF THE INVENTION

One aspect of genetic engineering involves the insertion of foreign DNA sequences derived from eucaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby effect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eucaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the $P_L$ promoter from λ bacteriophage. (Bernard, H. V., et al., Gene (1979) 5, 59; Derom, C., et al., Gene (1982) 17, 45; Gheysen, D., et al., Gene (1982) 17, 55; Hedgpeth, J., et al., Mol. Gen. Genet. (1978) 163, 197; Remaut, E., et al., (1981) Gene 15, 81 and Derynck, R., et al., Nature (1980) 287, 193. In addition, European Patent Application No. 041,767, published Dec. 16, 1981, describes expression vectors containing the $P_L$ promoter from λ bacteriophage. However, none of these references describe the use of the $C_{II}$ ribosomal binding site.

The use of a vector containing the $P_L$ promoter from λbacteriophage and the $C_{II}$ ribosomal binding site has been described. (Oppenheim, A. B., et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

Other vectors which contain the $\lambda P_L$ promoter and the $C_{II}$ ribosomal binding site have also been described (Courntey, M., et al., PNAS (1984) 81, 669-673; Lautenberger, J. A., et al., Gene (1983) 23, 75-84 and Lautenberger, J. A., et al., Science (1983) 221, 858-860). However, all of these vectors lead to the production of fused proteins which contain the amino terminal portion of the $C_{II}$ protein.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing $P_L$ from λbacteriophage, Nut and the $C_{II}$ ribosomal binding site to synthesize a "eucaryotic" polypeptide (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed.

Applicants are aware of the existence of a pending U.S. patent application in the name of M. Rosenberg filed under U.S. Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the $C_{II}$ ribosomal binding region has been altered (p3, line 27).

Pending, co-assigned U.S. patent application Ser. No. 514,188, filed Jul. 15, 1983, now abandoned, describes novel vectors useful for the expression of polypeptides in bacteria. These vectors include $P_LO_L$, N utilization site for binding antiterminator N protein, ribosomal binding site, ATG codon, restriction enzyme site for inserting the gene encoding the desired polypeptide, an origin of replication and a selectable marker. In these vectors the distance between the N utilization site and the ribosomal binding site is greater than about 300 base pairs. In addition, each of these vectors contains a specific ribosomal binding site which cannot be readily replaced. These vectors were not equally useful for expression of different polypeptides.

$T_1T_2$ rRNA transcription termination sequences have been described. (Brosius, J., et al., J. Mol. Biol. 148, 107 (1981)). The placement of $T_1T_2$ rRNA transcription termination sequences at the 3' end of a procaryotic gene and the expression of such gene under the control of a promoter have been described. (Amann, E., et al., Gene (1983) 25, 167; Zabeau, M., et al., The EMBO Journal (1982) 1, 1217).

The present invention relates to expression vectors which unexpectedly provide enhanced expression of different polypeptides. By employing different ribosomal binding sites in the vectors of this invention it is possible to achieve enhanced expression levels of different polypeptides relative to the levels achieved with the previous vectors. In addition, using the same ribosomal binding sites as in the previous vectors, it is possible to achieve enhanced expression of the same polypeptides. Moreover, by placing $T_1T_2$ rRNA transcription termination sequences at the 3' end of the gene encoding a polypeptide whose expression is desired, it is possible to increase the amount of desired polypeptide relative to the total polypeptide produced by a bacterial host.

SUMMARY OF THE INVENTION

This invention concerns an improved expression vector which upon introduction into a suitable bacterial host cell, e.g., *Escherichia coli*, containing the thermolabile repressor $C_I$ renders the host cell capable, upon increasing the temperature of the host cell to a temperature at which the repressor is inactivated, of effecting expression of a desired gene inserted into the vector and production of the polypeptide encoded by the gene comprising:

a double-stranded DNA molecule which includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA sequence;

and which additionally includes a DNA sequence which contains an origin of replication from a bacterial plasmid capable of autonomous replication in the host cell and a DNA sequence which contains a gene associated with a selectable or identifiable phenotypic trait which is manifested when the vector is present in the host cell, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs. Desirably, the $T_1T_2$ rRNA termination sequence is less than about 100 base pairs from the 3' end of the second restriction enzyme site, more desirably it is less than about 20 base pairs from the 3' end of the site. The presently preferred vector is p579.

Genes, e.g., cDNAs, encoding desired polypeptides, such as growth hormones, e.g., bovine, porcine, chicken or human growth hormones, human superoxide dismutase, human apolipoprotein E or analogs thereof, may be inserted into the second restriction enzyme site of the vector to create plasmids. The plasmids in turn can be introduced into suitable hosts where the genes can be expressed and the desired polypeptide produced The presently preferred plasmids are for bovine growth hormone (bGH), pHG44, pSAL 5600-1 and p7200-22; for porcine growth hormone (pGH), p3009; for chicken growth hormone (cGH), p5003; for human superoxide dismutase (SOD), pSOD$\beta_1$TT-1; and for human apolipoprotein E (ApoE), pTV-170, pTV-190, pTV-194 and pTV-214. Preferred hosts include *Escherichia coli* A1637, A1645, A2602, A2097 and A1563.

The resulting host vector systems can be employed to manufacture polypeptides. Host cells containing the plasmids are grown under suitable conditions permitting production of polypeptide and the resulting polypeptide is recovered. Using the host vector systems, analogs of human apolipoprotein E have been prepared.

DESCRIPTION OF THE FIGURES

The restriction maps for each of the plasmids shown in FIGS. 1-24 do not identify all restriction sites present on each plasmid. In some cases restriction sites are shown in one figure but not in another. However, in all cases those restriction sites necessary for a complete understanding of the invention are shown.

```
GGAATTCC
CCTTAAGG
``` was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

```
AATTCCCAGCCATG...
      GGGTCGGTAC...
``` at the 5' end. This sequence demonstrates that pALRI contains an EcoRI restriction site which includes the TTC codon for residue number 1 (phenylalanine) of natural bGH. pALRI was subjected to a partial cleavage with PstI. The digest was treated with DNA polymerase I large fragment (Klenow) and HindIII linkers with the sequence:

```
GAAGCTTC
CTTCGAAG
``` were attached by ligation. The ligation mixture was cleaved with EcoRI and HindIII. The fragment containing bGH cDNA was isolated and subcloned into pBR322 between the EcoRI and HindIII restriction sites to give pAL500 (ATCC No. 39782).

Figure 1:
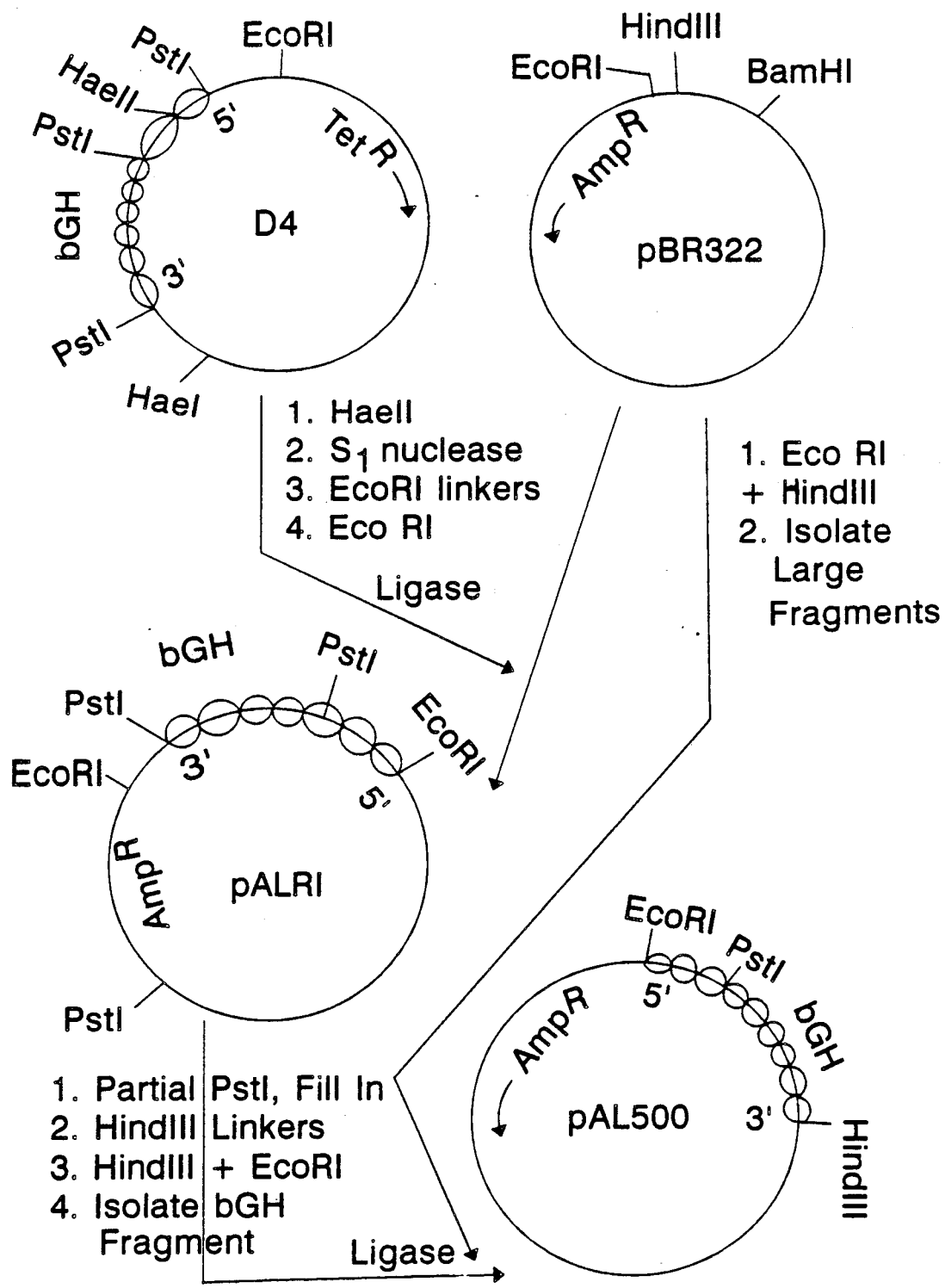
FIG. 1 Construction of pAL500. A plasmid containing bGH cDNA, D4 (ATCC No. 31826), was digested with HaeII. The resulting 1600 base pair large fragment was purified and digested at 37° C. for 5 minutes with S1 exonuclease. A synthetic EcoRI linker with the sequence.
Figure 2:
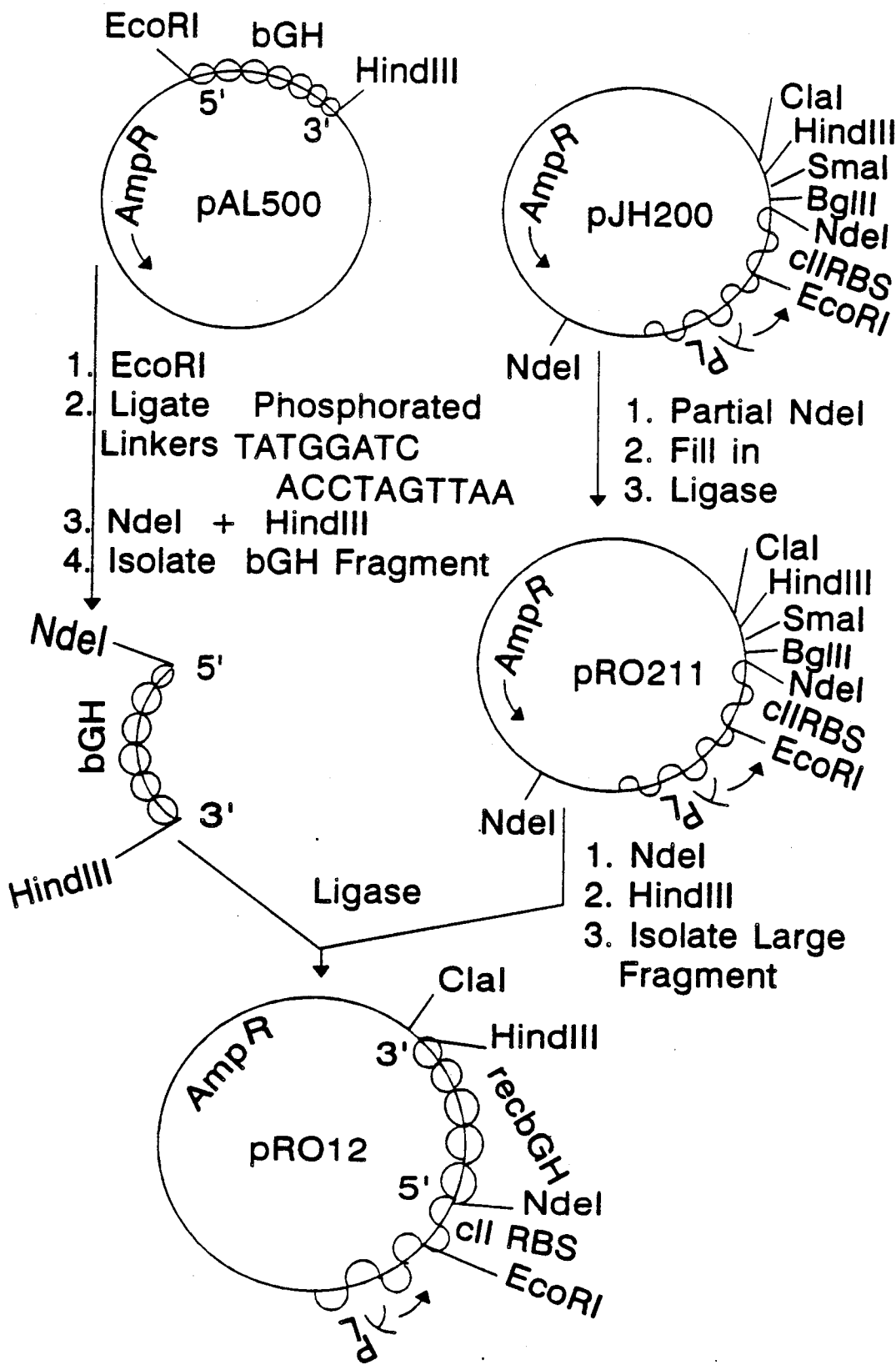

FIG. 2. Construction of pRO211 and pRO12. The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

```
TATGGATC
ACCTAGTTAA
```

The ligation mixture was digested with NdeI and HindIII and the resulting NdeI-HindIII bGH fragment isolated.)

Figure 3:
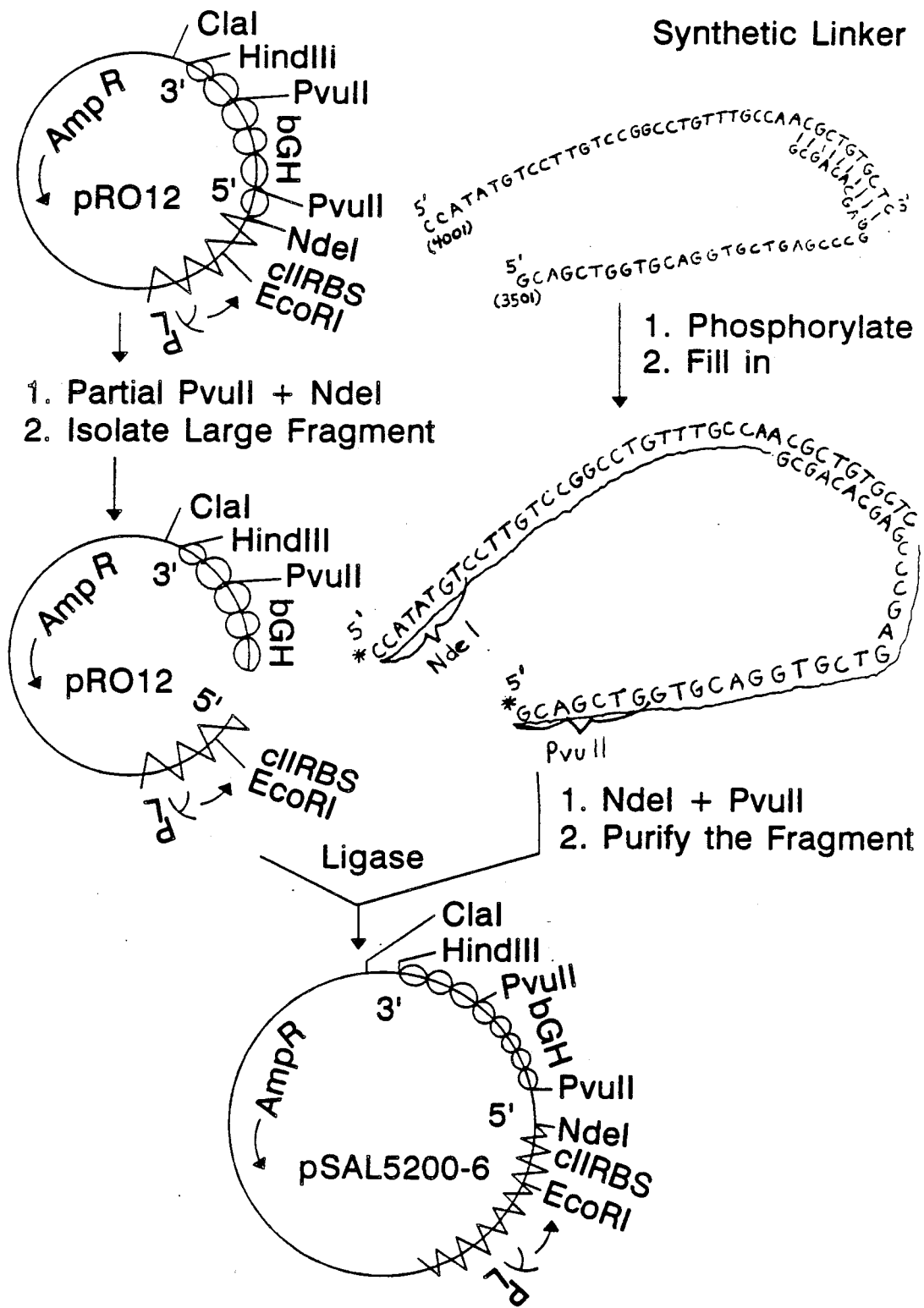

FIG. 3. Construction of pSAL 5200-6 pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

```
CCATATGTCCTTGTCCGGCCTGTTTGCCAACGCTGTGCTC-3'
          3'-GCGACACGAGGCCCGAGTCGTGGACGTGGTCGACG
```

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

Figure 4:
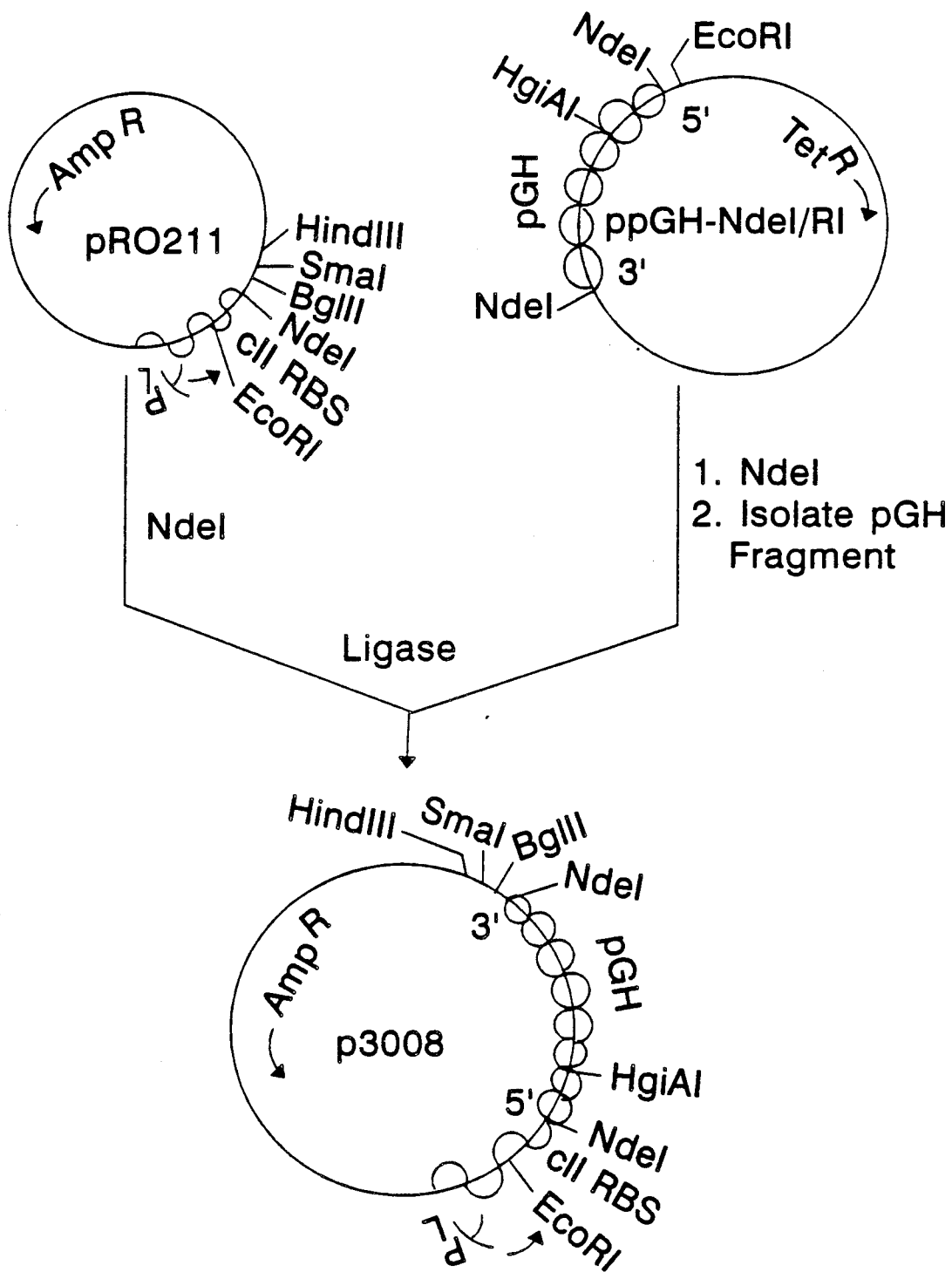

FIG. 4. Construction of p3008. p3008 (ATCC No.39804) was constructed by ligating NdeI-digested pRO211 [FIG. 2] with the pGH fragment isolated from an NdeI digest of the plasmid ppGH-NdeI/RI.

ppGH-NdeI/RI contains full length pGH cDNA to both ends of which NdeI sites have been added by means of synthetic linkers.

Figure 5:
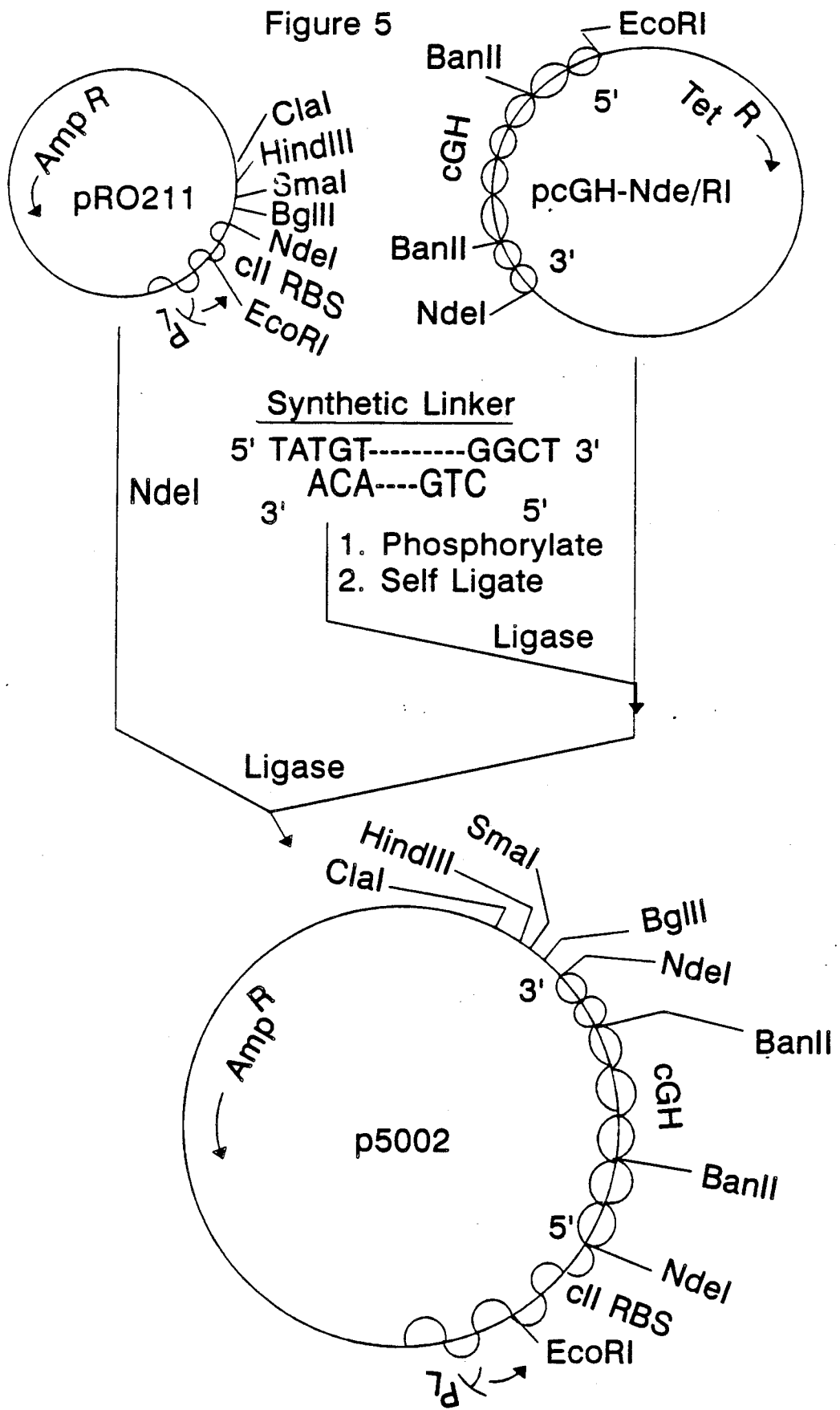

FIG. 5. Construction of p5002. p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence:

```
TATGTTCCCTGCCATGCCCCTCTCCAACCTGTTTGCCAACGCTGTGCTGAGGGCT
    ACAAGGGACGGTACGGGGAGAGGTTGGACAAACGGTTGCGACACGACTC
```

The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

Figure 6:
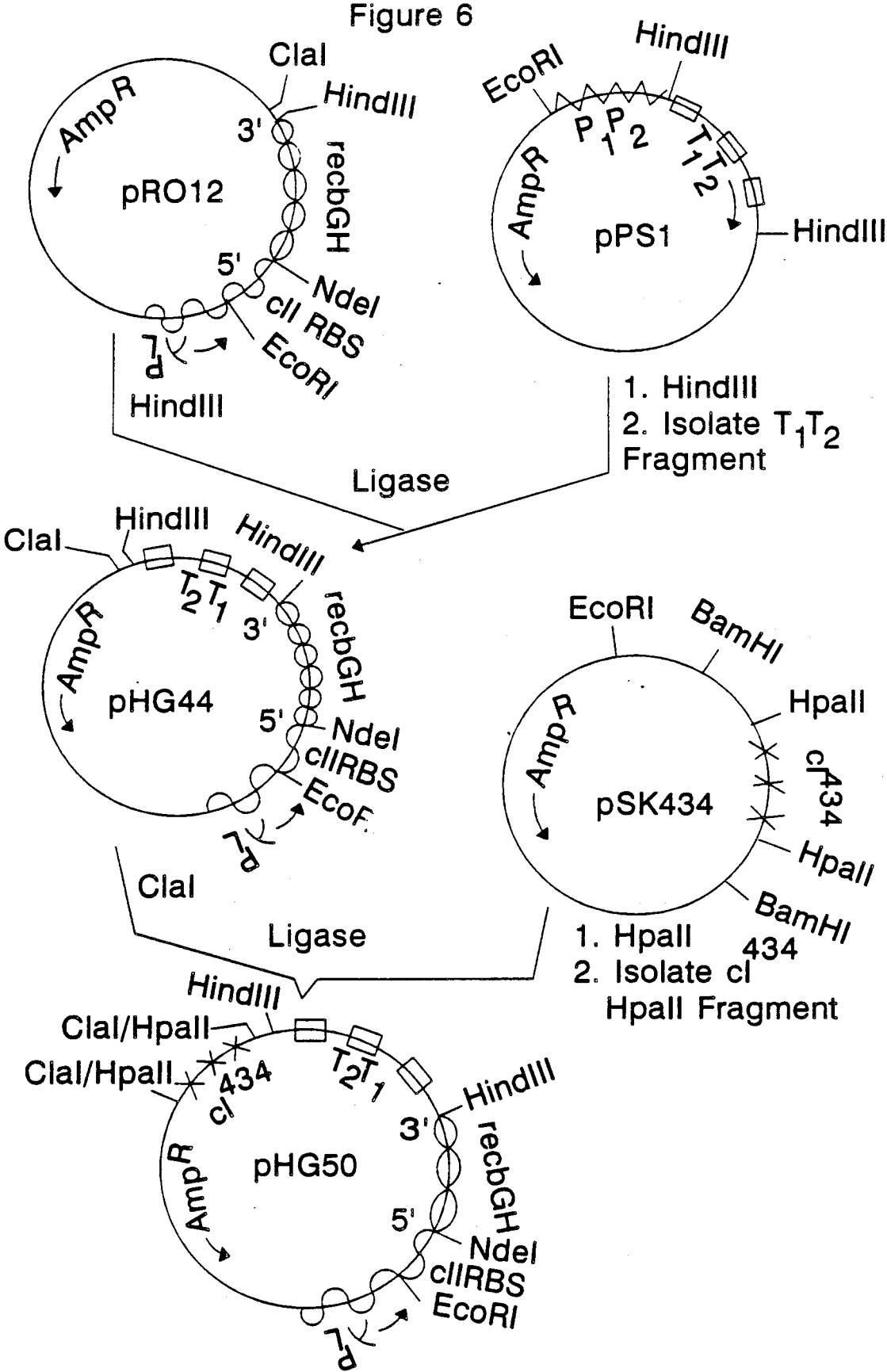

FIG. 6. Construction of pHG44 and pHG50. pRO12 (FIG. 2) was digested with HindIII. The linear form DNA (form III) was purified from agarose gel and ligated to a HindIII-HindIII fragment of about 1200 base pairs which contains the rRNA operon transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

Figure 7:
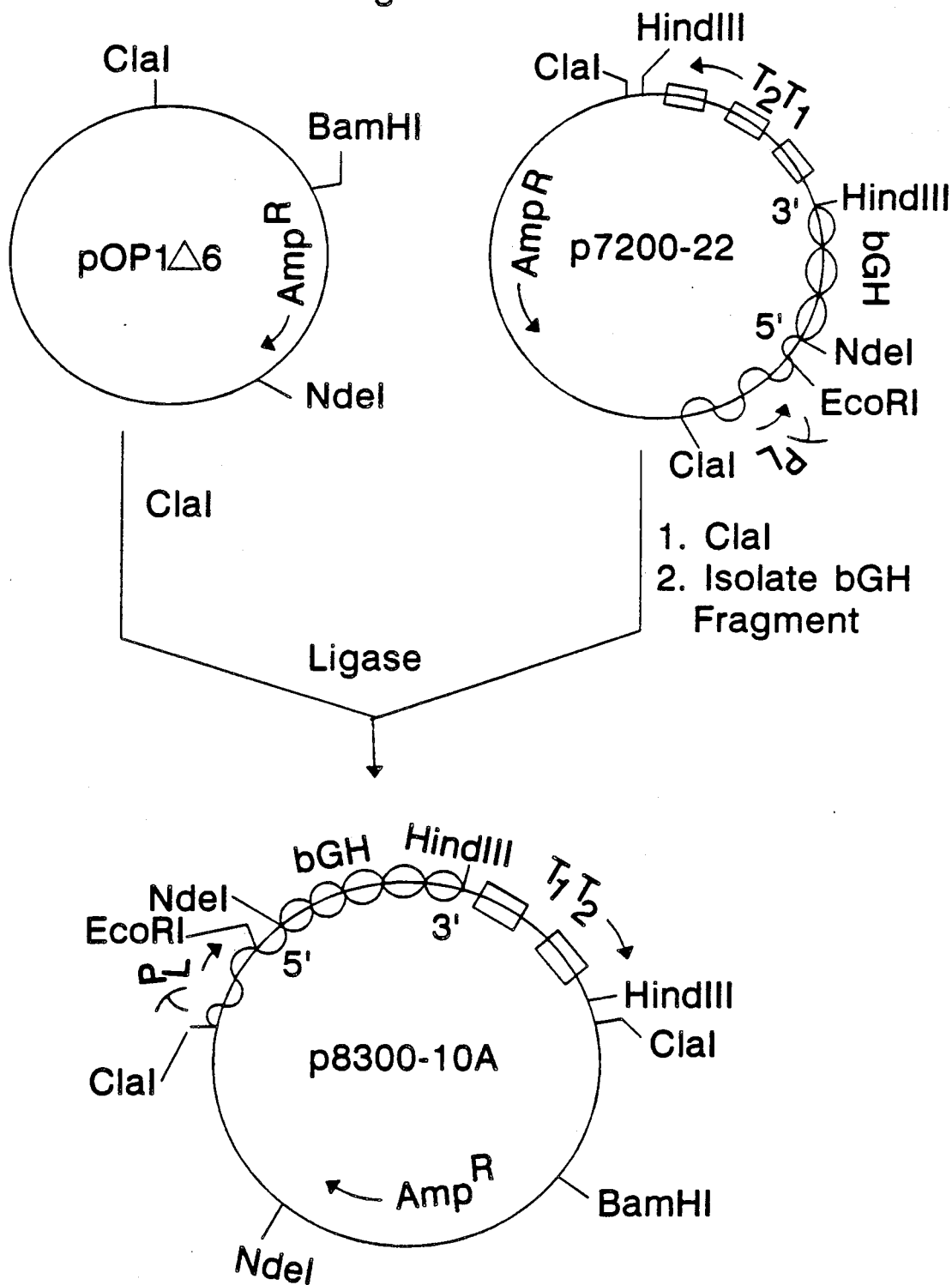

FIG. 7. Construction of p8300-10A. The plasmid p8300-10A (ATCC No. 39785) which expresses an analog of the natural phenylalanine form of bGH having methionine at the N-terminus (met-phe bGH) was prepared as follows. The plasmid p7200-22 contains the $\lambda P_L$ promoter and ribosomal binding site derived from pJH200 (ATCC No. 39783), DNA encoding met-phe bGH and the $T_1T_2$ rRNA termination sequences. The ClaI-ClaI fragment containing the $\lambda P_L$ promoter, the $C_{II}$ ribosomal binding site, the met-phe bGH gene and the $T_1$Thd transcription termination sequences was inserted into the unique ClaI site of plasmid pOP1Δ6, a constitutive high copy number plasmid, to form p8300-10A.

Figure 8:
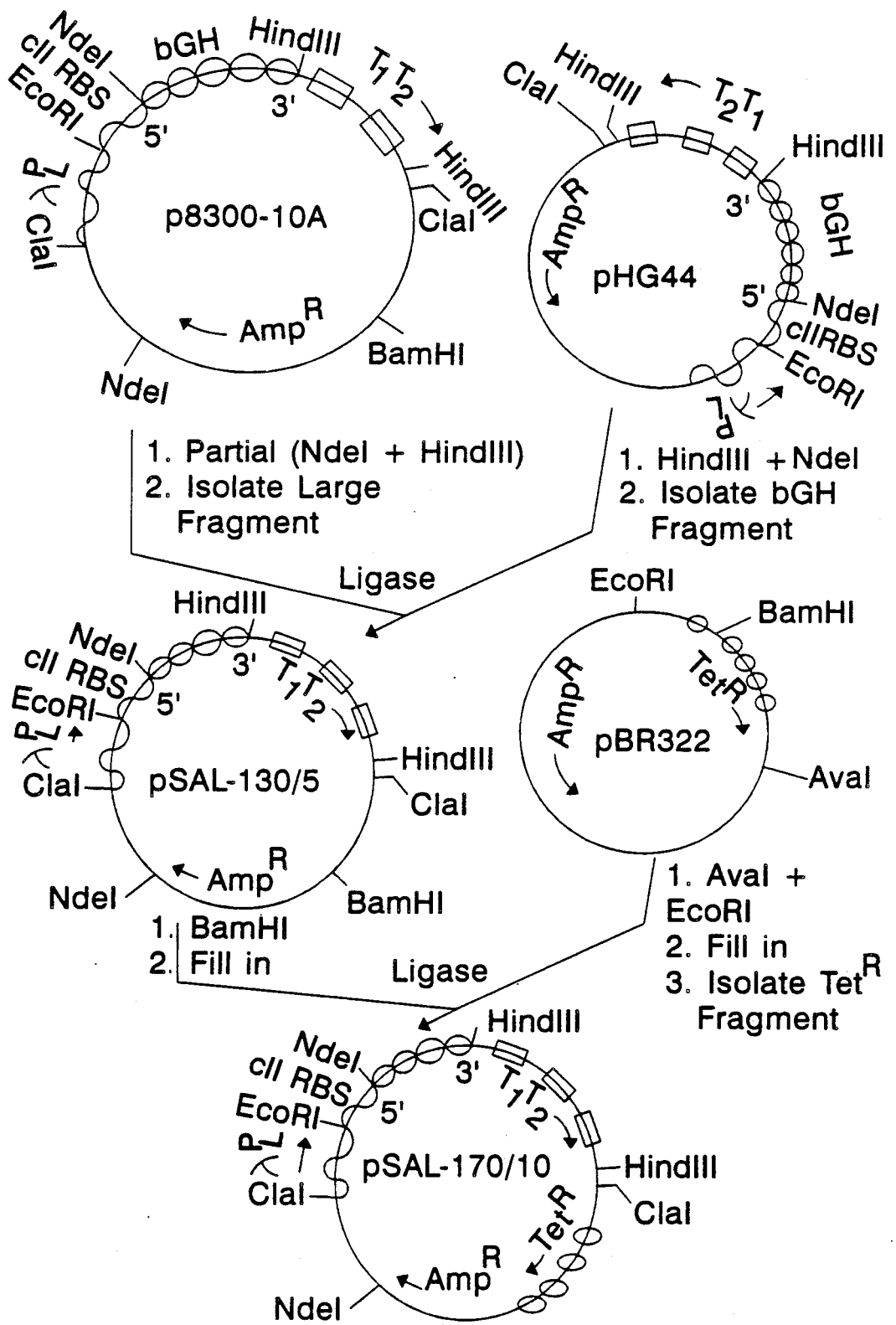

FIG. 8. Construction of pSAL-130/5 and pSAL-170/10. The plasmid pHG44 (ATCC No. 39806) expressing met-asp-gln bGH protein was digested with NdeI and HindIII. The resulting NdeI-HindIII bGH fragment was isolated and ligated to a fragment from p8300-10A (ATCC No. 39785) prepared by partial digestion with both NdeI and HindIII. Such a ligation replaces the met-phe bGH gene fragment with the met-asp-gln bGH gene fragment. The plasmid so obtained, pSAL-130/5, expresses rec bGH. pSAL-170/10 was obtained by treating the EcoRI-AvaI fragment containing the TetR gene of pBR322 plasmid (ATCC No.

37017) with DNA polymerase I (Klenow) and inserting it into pSAL-130/5 which had been digested with BamHI and filled in with DNA polymerase I (Klenow).

Figure 9:
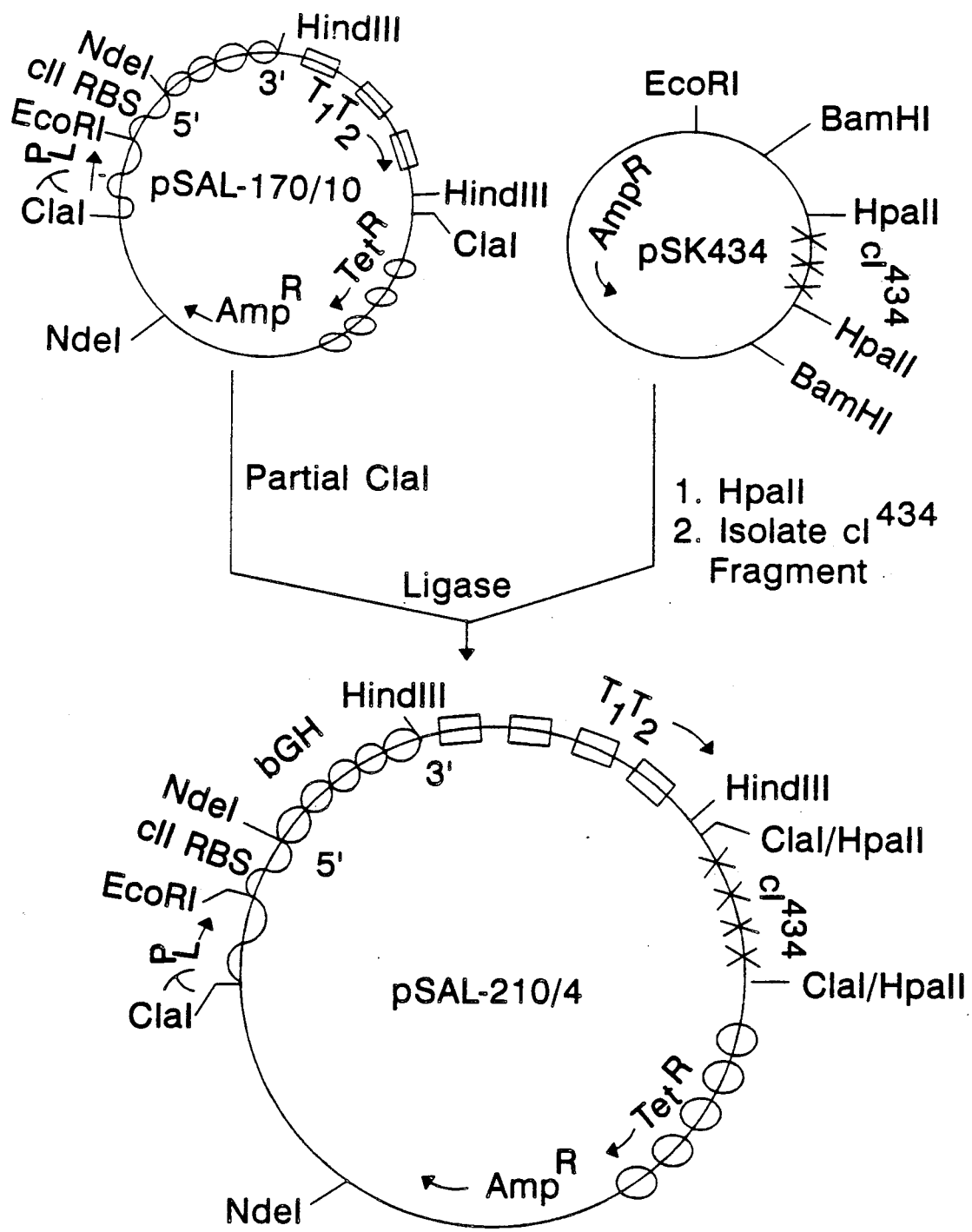

FIG. 9. Construction of pSAL-210/4. Linear form DNA (form III) was prepared by partial ClaI digestion of pSAL-170/10. It was purified from an agarose gel and ligated to a HpaII-HpaII cI$^{434}$ gene fragment which was isolated from a HpaII digest of the plasmid pSK434 (ATCC No. 39784).

Figure 10:
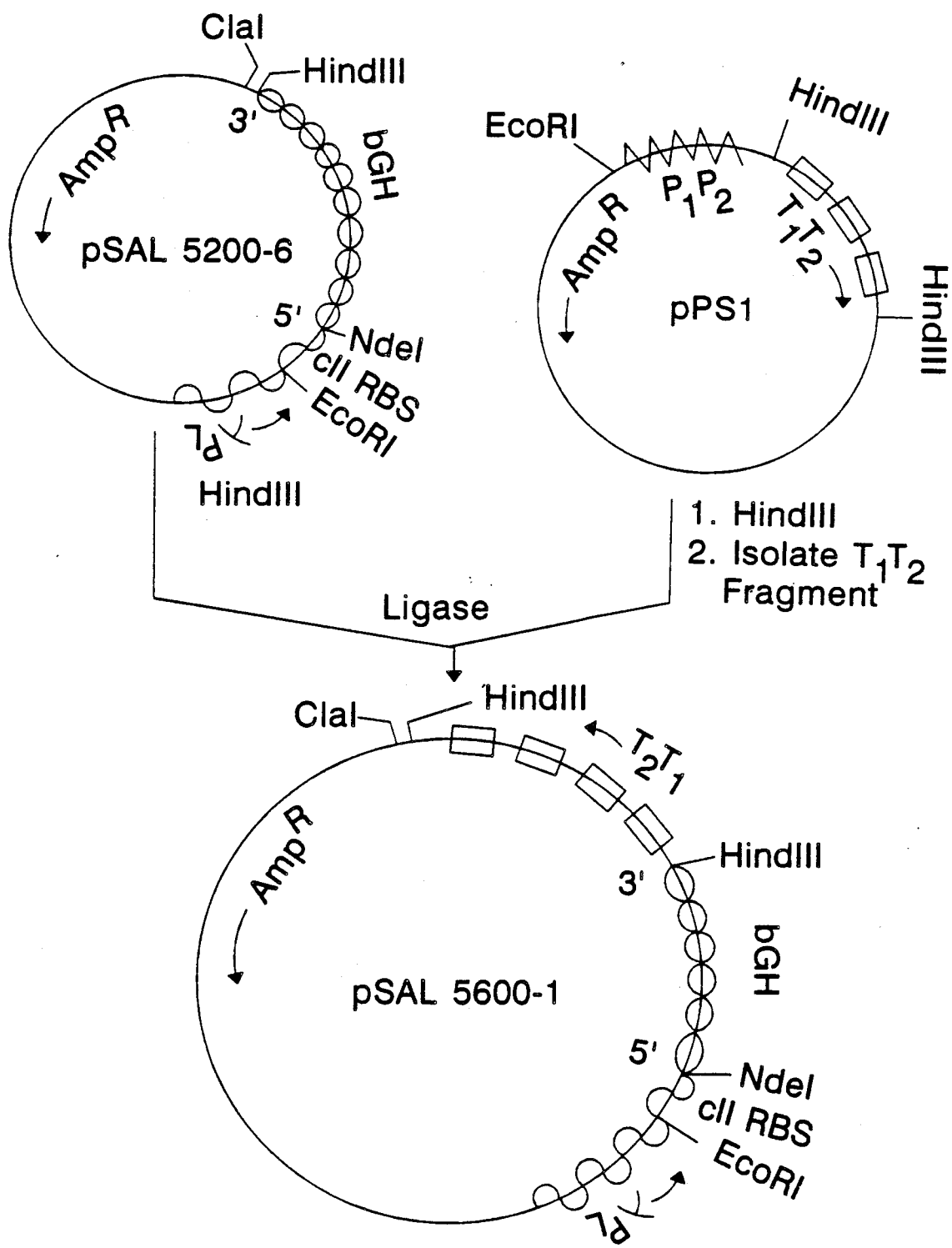

FIG. 10. Construction of pSAL 5600-1. pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, $T_1T_2$. The $T_1T_2$ HindIII-HindIII fragment was isolated from the plasmid pPS1 (ATCC No. 39807) which was digested with HindIII. The resulting plasmid pSAL 5600-1 contains the $T_1T_2$ sequences at the 3' end of the met-asp-gln bGH sequence.

Figure 11:
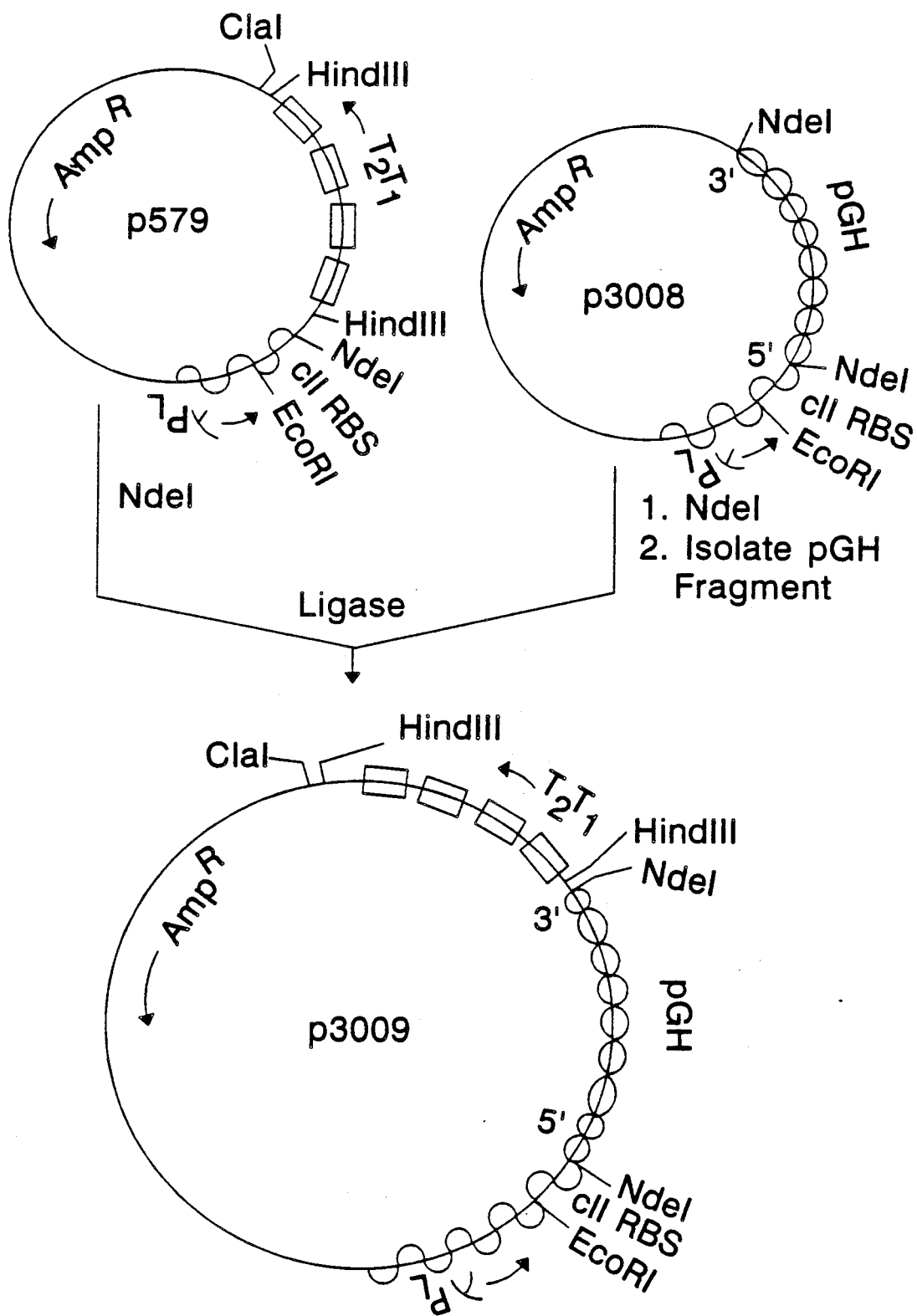

FIG. 11. Construction of p3009. The NdeI-NdeI pGH fragment was isolated from plasmid p3008 (ATCC No. 39804) (FIG. 5). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

Figure 12:
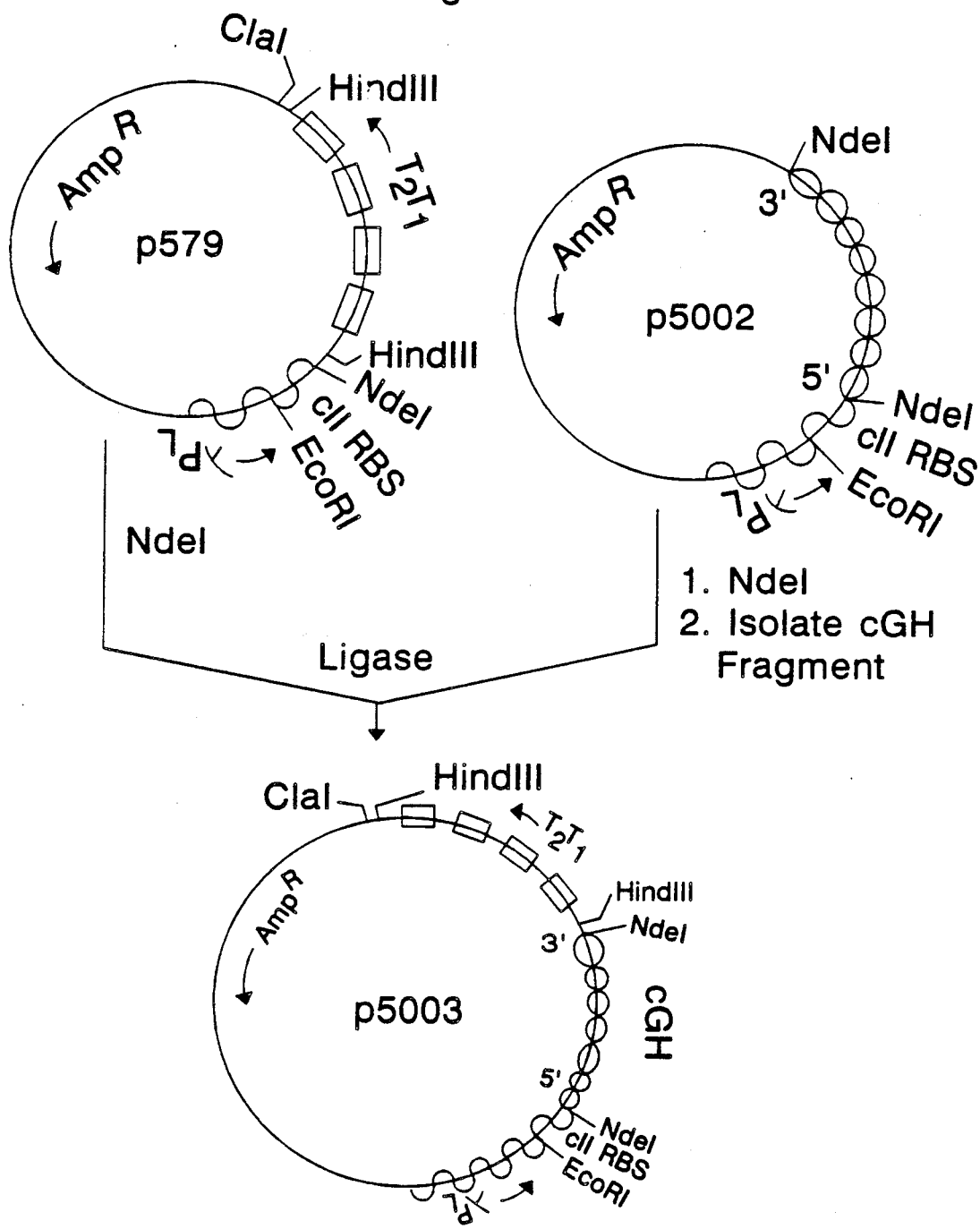

FIG. 12. Construction of p5003. The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

Figure 13:
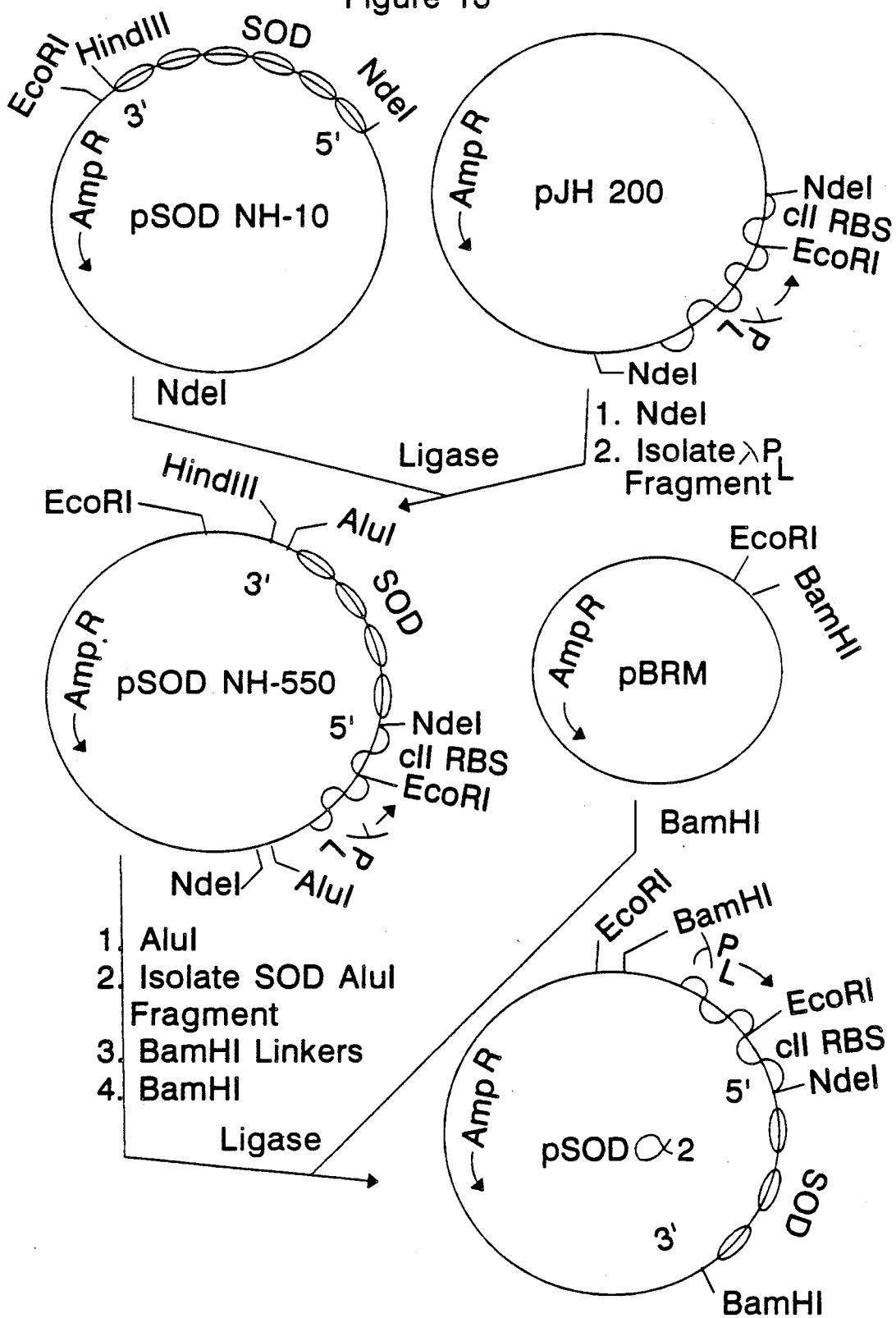

FIG. 13. Construction of pSODα2. The pJH200 (ATCC No. 39783) expression vector was digested with NdeI. The 550 base pair NdeI fragment containing the λP$_L$ promoter and C$_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79: 2808 ]) The resulting plasmid pSOD NH-550 was digested with AluI. (Only the relevant AluI site is shown in the figure.) The large AluI fragment containing the λP$_L$ promoter and the SOD gene was isolated. BamHI linkers were attached and the resulting fragment was digested with BamHI. The BamHI digestion product was inserted into the unique BamHI site of pBRM (ATCC No. 37283) to form pSODα2 (ATCC No. 39786).

Figure 14:
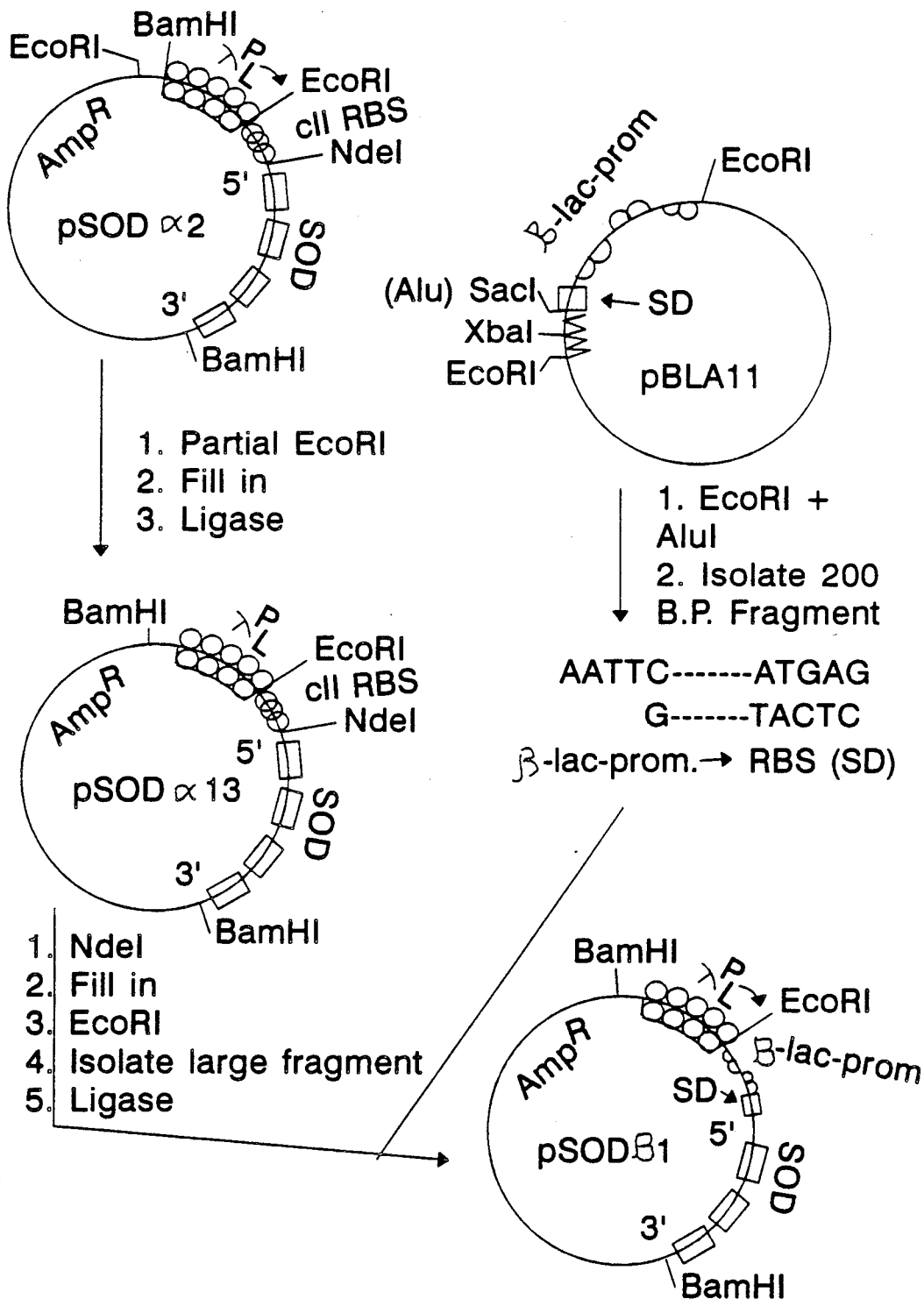

FIG. 14. Construction of pSODα13 and pSODβ1. The plasmid pSODα2 (ATCC No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODα1 contains the ribosomal binding site of the α-lactamase gene and the λP$_L$ promoter.

Figure 15:
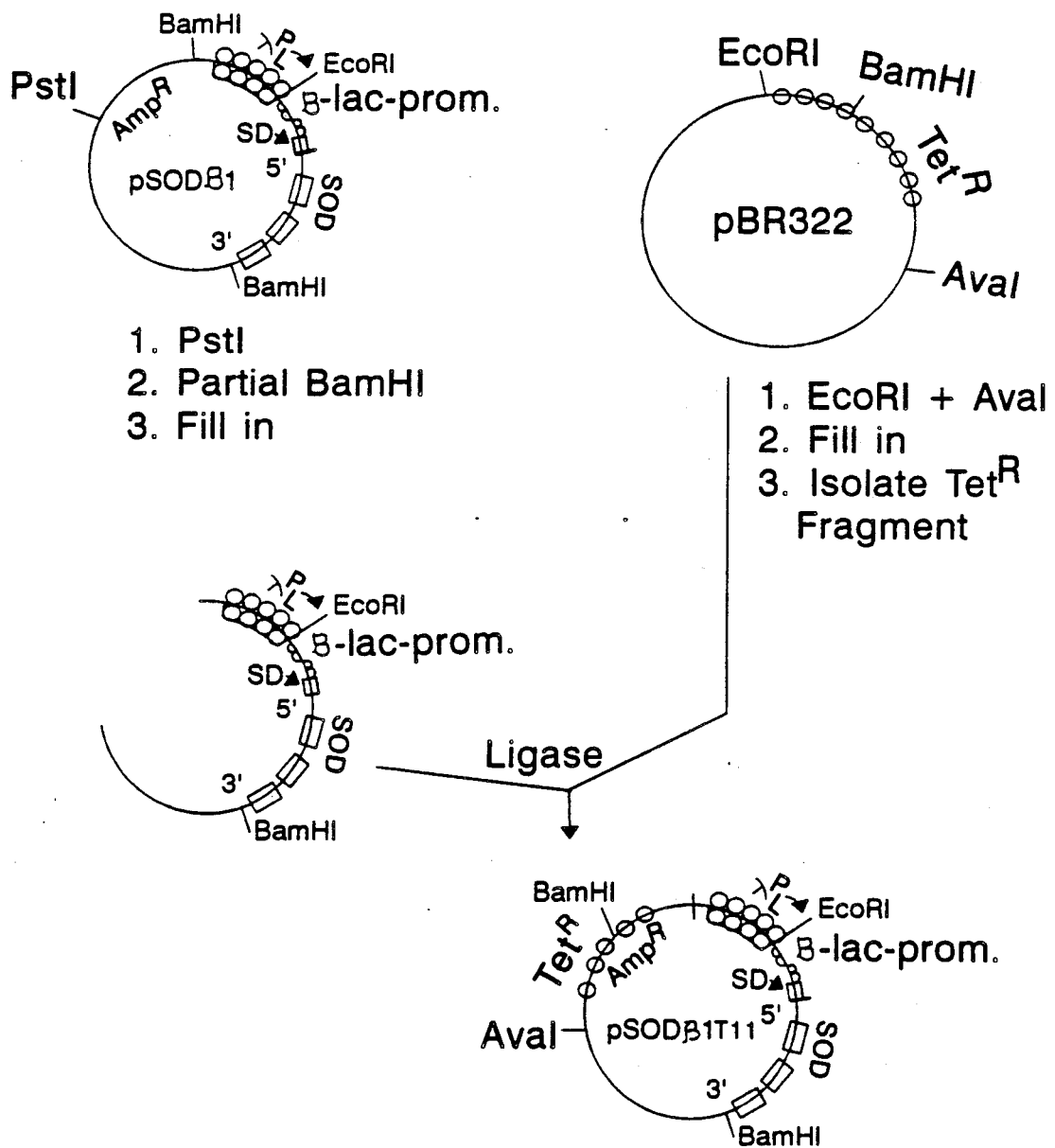

FIG. 15. Construction of pSODβ$_1$T$_{11}$. Plasmid pBR322 (ATCC No. 37017) was digested with EcoRI and AvaI. The resulting DNA was filled in with DNA polymerase I (Klenow). The Tet$^R$ gene fragment was then isolated and ligated to the large fragment isolated from pSODβ1 (FIG. 14) plasmid which had been digested with PstI followed by a partial BamHI digest and then filled in with DNA polymerase I (Klenow). The resulting plasmid pSODβ$_1$T$_{11}$ contains the TetR gene.

Figure 16:
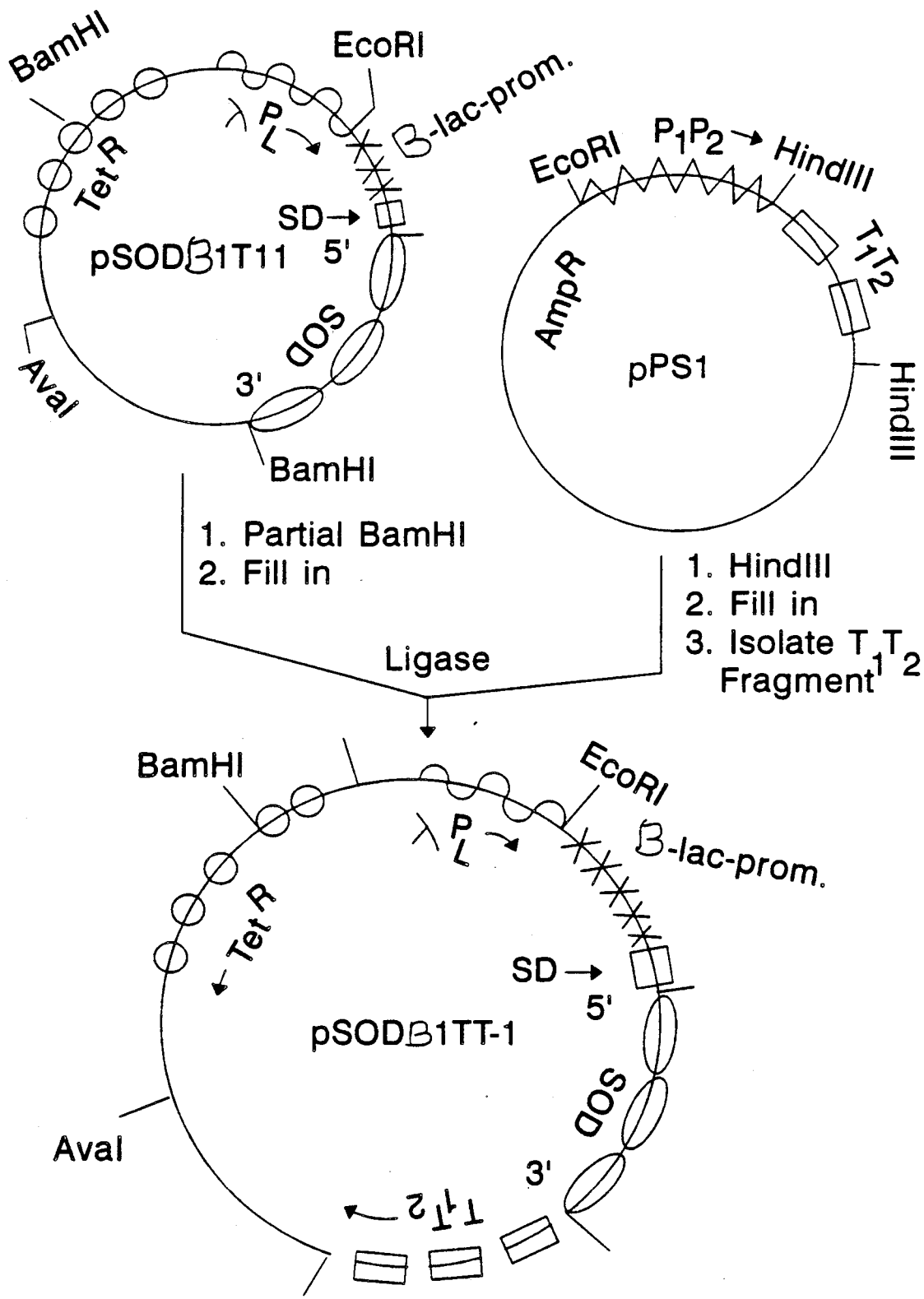

FIG. 16. Construction of pSODβ$_1$TT-1. The rRNA T1T2 transcription termination fragment was isolated from plasmid pPS1 (ATCC No. 39807) which had been digested with HindIII and filled in with DNA polymerase I (Klenow). The fragment was ligated to plasmid pSODβ$_1$T$_{11}$ (FIG. 15) which had been partially digested with BamHI and filled in with DNA polymerase I (Klenow).

Figure 17:
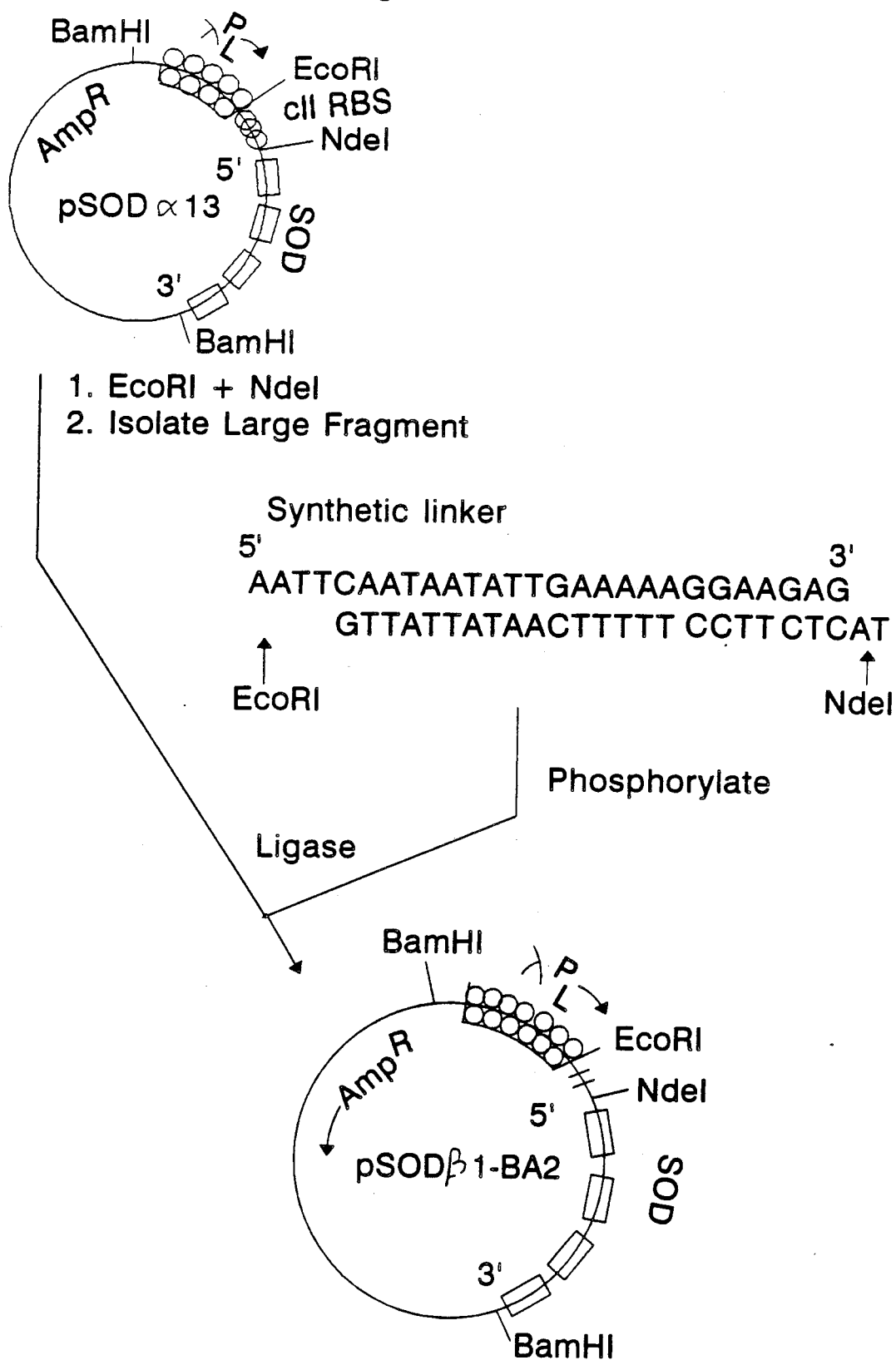

FIG. 17. Construction of pSODβ$_1$-BA2. A synthetic DNA fragment with the sequence:

5'-AATTCAATAATATTGAAAAAGGAAGAG-3'
    GTTATTATAACTTTTTCCTTCTCAT which is similar to the sequence of the natural β-lactamase ribosomal binding site, was phosphorylated and ligated to the large fragment of pSODα3 plasmid (FIG. 14) which had been digested with NdeI and EcoRI.

Figure 18:
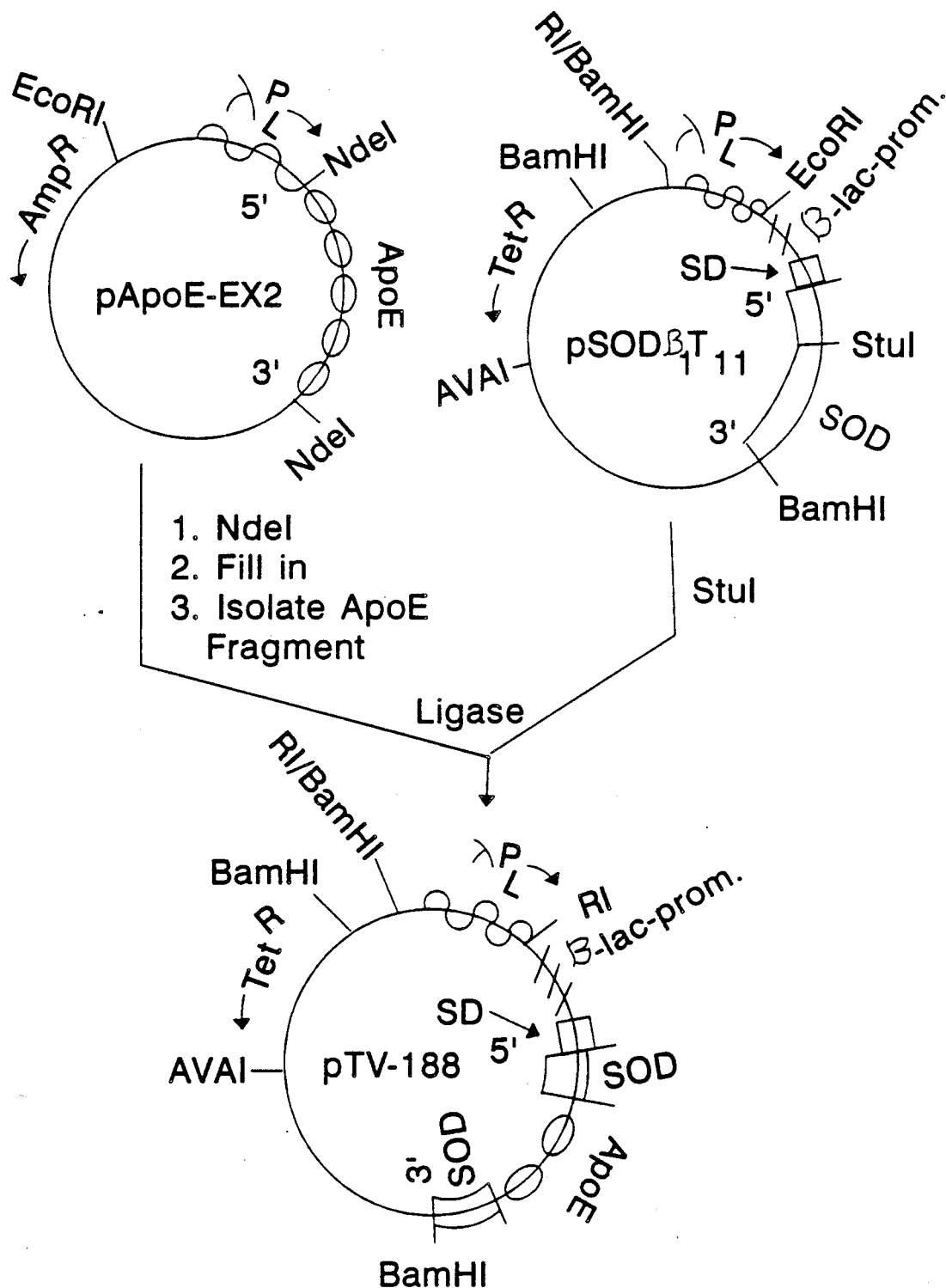

FIG. 18. Construction of pTV-188. Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSODβ$_1$T$_{11}$ plasmid (FIG. 15). The resulting plasmid pTV-188 expresses an ApoE fused protein.

FIG. 19. Construction of p579. The rRNA operon T1T2 transcription termination fragment was isolated from plasmid pPS1 (ATCC No. 39807) which had been digested with HindIII. The T$_1$T$_2$ fragment was inserted into the unique HindIII site of pRO211 (FIG. 2) which had been digested with HindIII. The resulting expression vector, p579, contains the λP$_L$ promoter, the C$_{II}$ ribosomal binding site, followed by the T$_1$T$_2$ transcription termination signals.

Figure 20:
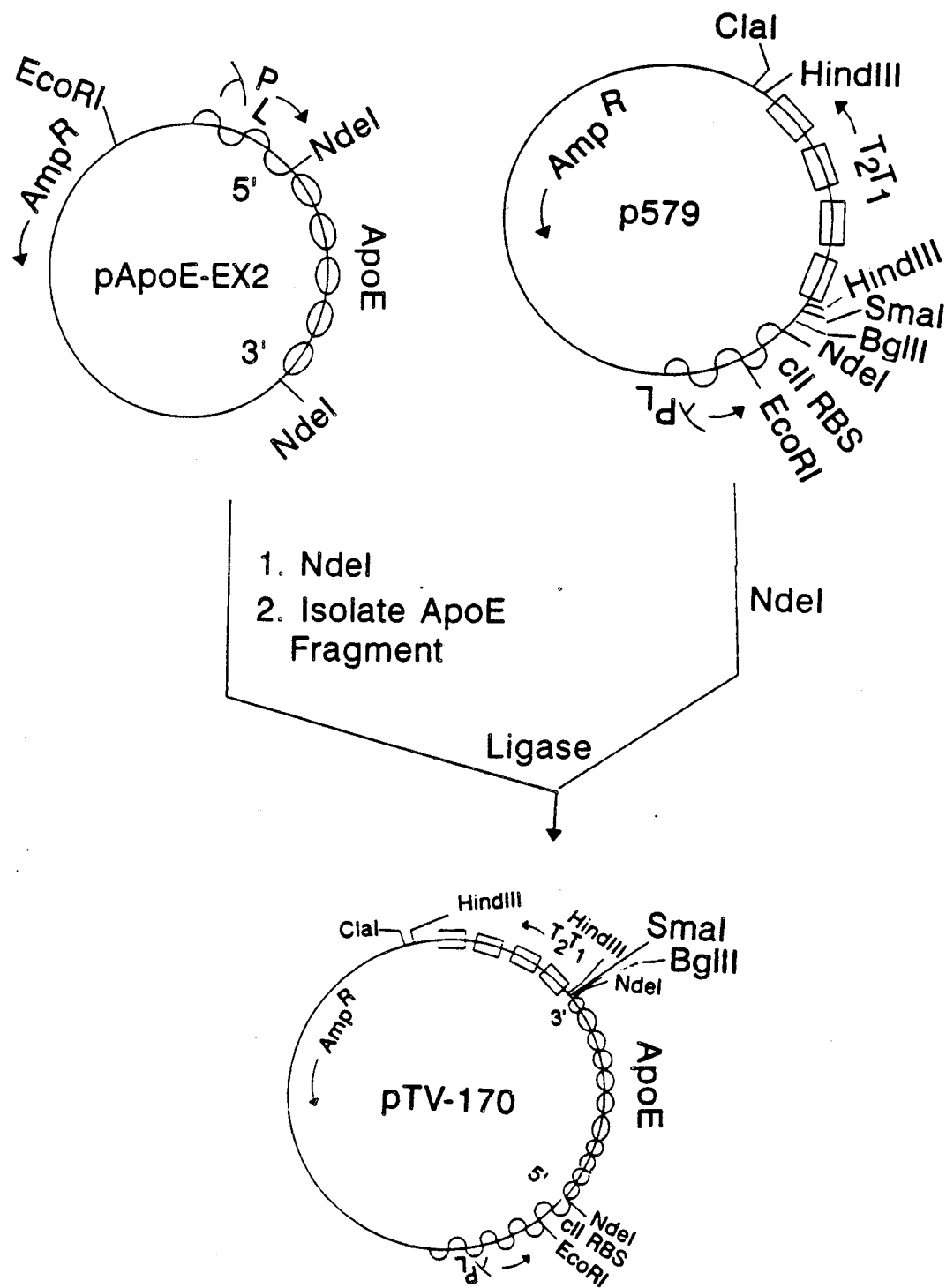

FIG. 20. Construction of pTV-170. The NdeI-NdeI ApoE fragment was isolated from plasmid pApoE-EX2 (ATCC No. 39787) and inserted into the unique NdeI site of the expression vector p579 (FIG. 19) which had been digested with NdeI. The resulting plasmid pTV-170 expresses an analog of natural human ApoE protein having a methionine residue added at the N-terminus.

FIG. 21. Construction of pTV-190. The plasmid pTV-170 (FIG. 20) was partially digested with NdeI and filled in with DNA polymerase I (Klenow). The isolated linear form DNA was religated to yield the plasmid pTV-190 which was analyzed and found to have only one NdeI site at the 5' end of the ApoE gene.

Figure 22:
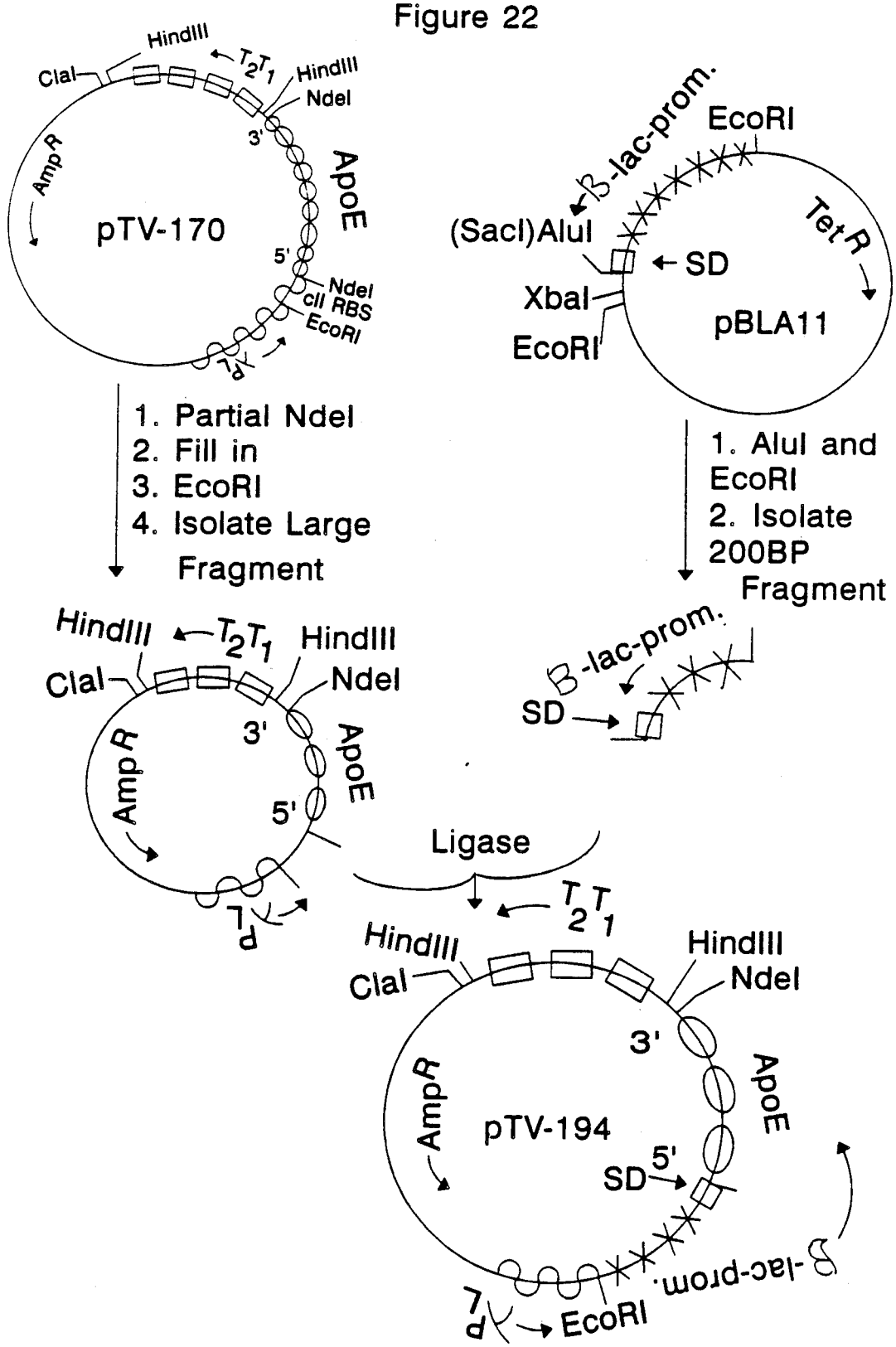

FIG. 22. Construction of pTV-194. The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

Figure 23:
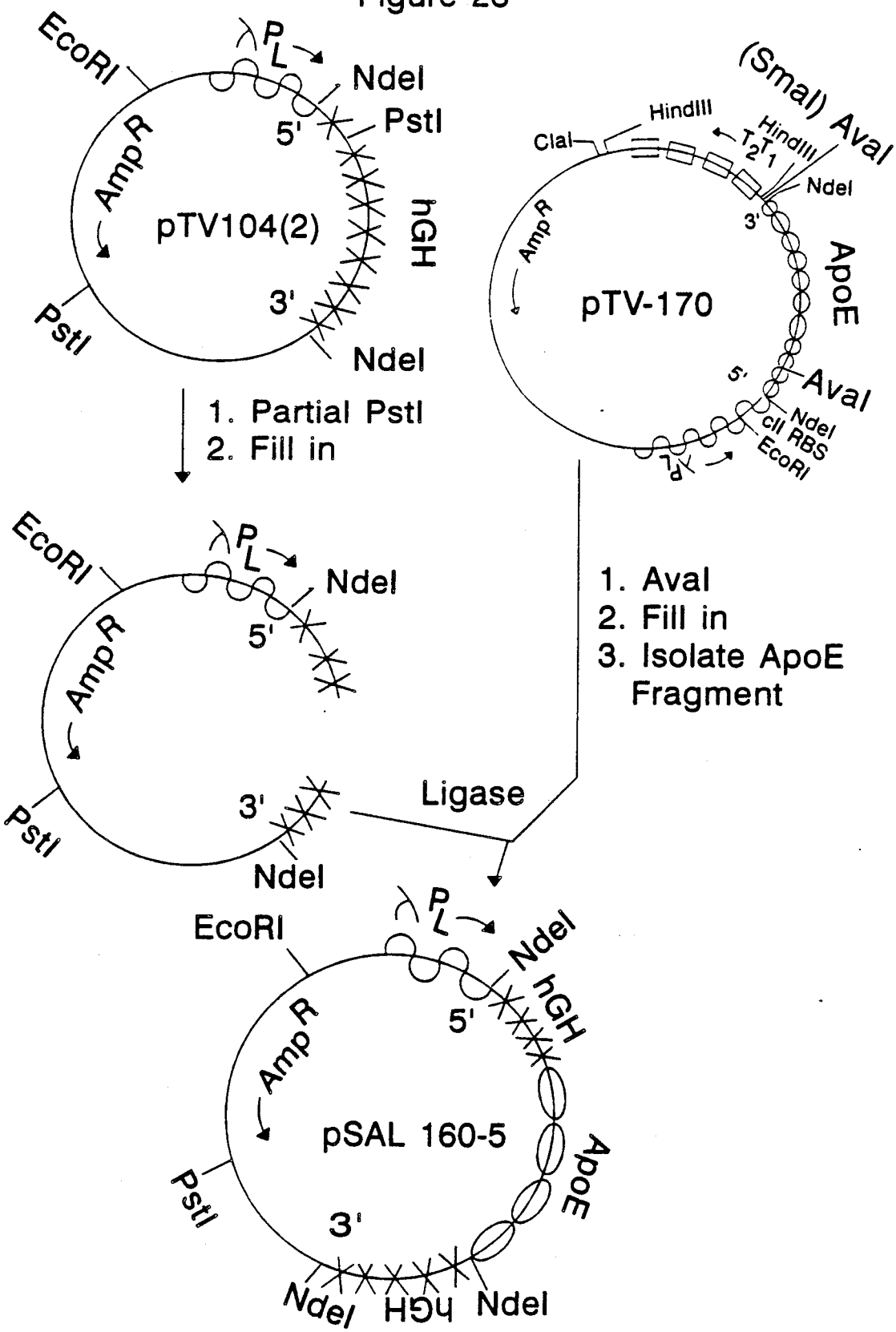

FIG. 23. Construction of pSAL 160-5. An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site cf the pTV 104(2) plasmid (ATCC No. 39384) which was partially digested with PstI and filled in with DNA Polymerase I (Klenow). The resulting plasmid is designated pSAL 160-5.

Figure 24:
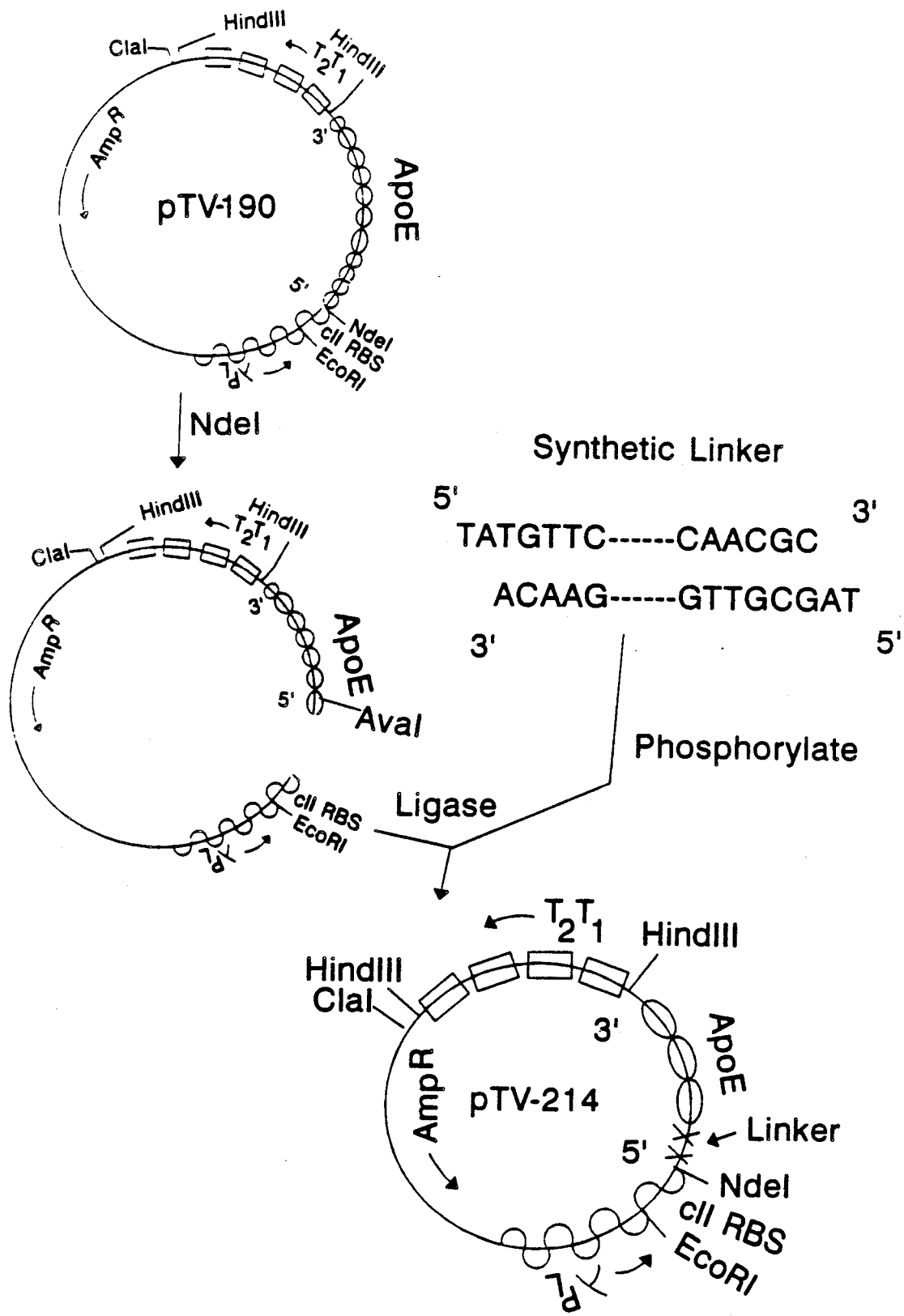

FIG. 24. Construction of pTV-214. A synthetic fragment containing the first 14 amino acids of human growth hormone with the sequence:

```
TATGTTCCCAACCATTCCATTATCCCGTCTGTTCGACAACGC
    ACAAGGGTTGGTAAGGTAATAGGGCAGACAAGCTGTTGCGAT
``` was phosphorylated using $\gamma$-$^{32}$P-ATP and polynucleotide kinase. The phosphorylated linker was inserted into the unique NdeI site of pTV-190 plasmid which had been digested with NdeI.

DETAILED DESCRIPTION OF THE INVENTION

A vector has been developed which enables the achievement of enhanced levels of gene expression and polypeptide production. The vector is a double-stranded DNA molecule. Upon introduction into a suitable bacterial host cell containing the thermolabile repressor $C_I$ the vector renders the host cell capable, upon increasing the temperature of the host cell to a temperature at which the repressor is inactivated, of effecting expression of a desired gene inserted into the vector and production of polypeptide encoded by the gene.

The vector includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA transcription termination sequence.

The vector also includes a DNA sequence which contains an origin of replication from a bacterial plasmid capable of autonomous replication in the host cell and a DNA sequence which contains a gene associated with a selectable or identifiable phenotypic trait which is manifested when the vector is present in the host cell. The distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs.

Another component of the vector is a first restriction enzyme site permitting replacement of the DNA sequence containing the ribosomal binding site which follows thereafter. Numerous such sites may be used. Suitable sites include EcoRI.

Yet another component of the vector is a second restriction enzyme site for insertion of desired genes into the vector in phase with the ATG initiation codon. Numerous such sites may be used. Suitable sites include NdeI, ClaI, HindIII, SmaI, BglII, XbaI, SacI and AluI.

Generally it is desirable that the second restriction enzyme site also function as the second restriction site necessary to permit replacement of the DNA sequence containing the ribosomal binding site. If the second restriction site is not also used for this purpose then the vector of this invention must also include a third restriction enzyme site after the ribosomal binding site but prior to the second restriction site.

Preferably the vector contains two unique restriction enzyme sites The first site permits replacement of the DNA sequence containing the ribosomal binding site. The second site permits insertion of the desired gene into the vector in phase with the ATG initiation codon. In a presently preferred embodiment, EcoRI is the first restriction enzyme site and NdeI is the second restriction enzyme site.

A further component of the vector is a $T_1T_2$ rRNA transcription termination sequence Preferably, the $T_1T_2$ rRNA transcription termination sequence is less than about 100 base pairs from the 3' end of the second restriction enzyme site. More preferably, the $T_1T_2$ rRNA transcription termination sequence is less than about 20 base pairs from the 3' end of the second restriction enzyme site.

The preferred host for use with the vector is *Escherichia coli*. The presently preferred strains are A1637, A1645, A2602, A2097 and A1563. A2097 is presently the most preferred strain for the expression of the gene which produce:

1) an analog of bGH having the amino acid sequence met-asp-gln added to the amino-terminus of the phenylalanine form of authentic bGH; or
2) an analog of cGH having the amino acid methionine added to the amino-terminus of the phenylalanine form of natural cGH.

A1645 is presently the most preferred strain for expression of other genes. These strains have been deposited with the American Type Culture Collection in Rockville, Maryland, U.S.A. containing various plasmids as described more fully hereinafter. All such deposits were made pursuant to the Budapest Treaty on the International Recognition of the Deposit of Microorganisms except that pBR322 and pBRM are freely available from the American Type Culture Collection as ATCC Nos. 37017 and 37283, respectively, and D4 was deposited under ATCC No. 31826 in connection with the filing of a U.S. patent application.

A1645 was obtained from A1637 by selection for Gal+(ability to ferment galactose) as well as loss of tetracycline resistance. It still contains the lambda expression system but part of the transposon has been removed by selection. Its phenotype is C600 r−m+gal+thr−leu−lac− b1 ($\lambda$cI857 $\Delta$H1 $\Delta$Bam N+).

A2602 and A1563 are derived from SA500. Their phenotypes are SA500 his⁻ile⁻gal⁺Δ8(λCI857ΔH1 ΔBam N+) and SA500 his⁻ ile⁻ gal⁺ Δ8 lac ZxA21 (λcI859 int2 xis1 nutL3 ΔH1), respectively. A2097 is derived from A1645. Its phenotype is A1645 lac ΔχA21 proC:Tn10.

Preferably, the vector is a covalently closed circular double-stranded molecule. However, it is not essential that the vector be covalently closed.

The vector achieves its enhanced expression levels after the host cell is heated to a temperature at which the $C_I$ repressor protein is destroyed. A temperature above about 38° C. is effective for this purpose and since it is desired that unnecessary heat damage to the host cells be avoided to as great an extent as possible, it is generally desirable that the temperature not exceed 42° C. by more than a few degrees. One important component of the vector is the ribosomal binding site. Suitable sites are $C_{II}$ from lambda bacteriophage having the sequence:

TAAGGAAATACTTACAT
ATTCCTTTATGAATGTA;

a mutant of $C_{II}$ from lambda bacteriophage having the sequence:

TAAGGAAGTACTTACAT
ATTCCTTCATGAATGTA;

the major head protein gene of bacteriophage lambda having the sequence:

TTTTTTTACGGGATTTTTTTATG
AAAAAAATGCCCTAAAAAAATAC;

the natural β-lactamase ribosomal binding site derived from pBR322;

a synthetic oligonucleotide having the sequence:

AATTCGAGCGCAAGGAAACAGGCTCA
GCTCGCGTTCCTTTGTCCGAGTAT;

a synthetic oligonucleotide having the sequence:

AATTCAATAATATTGAAAAAGGAAGAG
GTTATTATAACTTTTTCCTTCTCAT; and a natural ribosomal binding site derived from *Bacillus thurengensis*.

The vector also includes an origin of replication from a bacterial plasmid capable of autonomous replication in the host cell. Suitable such origins of replication may be obtained from a number of sources, e.g. from pBR322 or pR1.

A DNA sequence which contains a gene associated with a selectable or identifiable phenotypic trait which is manifested when the vector is present in the host cell is also a component of the vector. Suitable genes include those associated with temperature sensitivity or drug resistance, e.g., resistance to ampicillin, chloroamphenical or tetracycline.

Relative to vectors described previously, the vectors of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoliprotein E or analogs of any of the preceding. By analog is meant a polypeptide having the same activity as the naturally occurring polypeptide but having one or more different amino acids added or deleted, or both, at the N-terminus of the polypeptide.

The vector may be formed by methods well known to those of ordinary skill in the art to which the invention relates. Such methods are described in greater detail in various publications identified herein, the contents of which are hereby incorporated by reference into the present disclosure in order to provide complete information concerning the state of the art.

The vectors of this invention may be engineered to yield plasmids which produce a recombinant bovine growth hormone. One example is the production of an analog of bGH which has the amino acid sequence met-asp-gln added to the amino terminus of the phenylalanine form of authentic bGH. Plasmid pHG44, which produces such a hormone, was constructed according to the scheme in FIG. 6 and was deposited in strain A2097 under ATCC No. 39806.

Another example is the production of an analog of bGH having the amino acid methionine added to the amino terminus of the phenylalanine form of natural bGH. Plasmid pSAL 5600-1, which produces such a hormone, was constructed according to the scheme in FIG. 10. Plasmid p7200-22 also produces such a hormone. This plasmid has a restriction map shown in FIG. 7.

One presently preferred vector is p579 which has the restriction map shown in FIG. 19. This vector can be introduced into suitable *Escherichia coli* strain, e.g. A1637, A2602, A1563, A1645 or A2097, using a conventional transformation method known to those of ordinary skill in the art. A gene encoding a desired polypeptide, e.g. porcine growth hormone or chicken growth hormone may be inserted into p579.

Porcine growth hormone cDNA has been inserted into p579 by digesting the vector with NdeI and ligating the open strand to pGH cDNA obtained from p3008 (ATCC No. 39804). The resulting plasmid is designated p3009. Its restriction map is shown in FIG. 11.

Chicken growth hormone cDNA has been inserted into p579 by digesting the vector with NdeI and ligating the open strand to cGH cDNA obtained from p5002. The resulting plasmid is designated p5003 and has a restriction map shown in FIG. 12. p5003 has been deposited in *Escherichia coli* strain A2097 under ATCC No. 39792.

The gene for the production of human apoliprotein E (ApoE3), presumably with the amino acid methionine added to the amino terminus in the final product, can also be inserted into p579. The construction of the resulting plasmid, designated pTV-170, is shown in FIG. 20. This plasmid contains the $C_{II}$ ribosomal binding site derived from pJH200 (ATCC No. 39783).

Plasmid pTV-170 can be modified by removal of one of the NdeI sites bounding the ApoE gene. The resulting plasmid, designated pTV-190, is shown in FIG. 21.

pTV-170 can also be modified by replacement of the $C_{II}$ ribosomal binding site with the 8 -lactamase promoter and Shine-Dalagarno ribosomal binding site sequence isolated from pBLAll (ATCC No. 39788). The resulting plasmid, designated pTV-194, has the restriction map shown in FIG. 22.

pTV-190 (FIG. 21) can be modified so that it produces an analog of human ApoE3 which has at its amino terminus the 14 amino acid amino terminus sequence of human growth hormone, followed by methionine, attached to the sequence of mature human ApoE3. Such a plasmid is designated pTV-214 and has a restriction map shown in FIG. 24.

The vectors of this invention may also be engineered to yield plasmids which produce an analog of human Cu-Zn superoxide dismutase (SOD) which differs from natural human SOD in that the amino terminus is not acetylated. Such a plasmid has been constructed according to FIG. 16 and has been designated pSOD$\beta_1$TT-1.

Using the same approach other plasmids may be prepared by inserting into the second restriction enzyme site of a vector according to the invention a gene encoding a desired polypeptide.

The preceding specific host vector systems involve E. coli A1637, A1645, A2606, A2097 and A1563. These host vector systems may be used to produce different polypeptides such as bovine, porcine, chicken and human growth hormones, superoxide dismutase and human apolipoprotein E. To do so, the host vector system is grown under suitable conditions permitting production of polypeptide which is then recovered.

Suitable conditions involve growth of the host vector system for an appropriate period of time at about 42° C. Desirably, the period of growth at 42° C. for all host vector systems except those designed to produce human apolipoprotein E is about 1 to 5 hours. The period of growth for host vector systems designed to produce human apolipoprotein E is desireably about 15 minutes.

By means of the preceding method a number of bGH, pGH, cGH, ApoE and SOD analogs have been prepared.

An analog of human apolipoprotein E has been prepared which has the amino acid sequence of human apolipoprotein E to the N-terminus of which the 14 amino acid N-terminal sequence of human growth hormone is attached, followed by methionine.

Veterinary compositions may be prepared which contain effective amounts of one or more bGH, cGH or pGH analog and a suitable carrier. Such carriers are well known to those of ordinary skill in the art. The analogs may be administered directly or in the form of a composition to a cow in order to increase milk or meat production, to a chicken in order to increase meat production or to a pig in order to increase meat production.

Pharmaceutical compositions may be prepared which contain effective amounts of one or more SOD or ApoE analog and a suitable carrier. Such carriers are well known to those skilled in the art. The analogs may be administered directly or in the form of a composition to a human subject, e.g., to treat deficiencies in SOD or ApoE production by the subject, or in the case of SOD to treat inflammation or other disorders for which human superoxide dismutase is indicated or in the case of ApoE to treat atherioscelerosis.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those of ordinary skill in the art and are described in numerous publications including by way of example the following:

T. Maniatis, E. F. Fritsch and J. Sambrook, *Molecular Cloning; A Laboratory Manual*, Cold Spring Harbor Laboratory, New York (1982).

*Methods in Enzymology*, vol. 65, "Nucleic Acids (Part 1)," edited by Lawrence Grossman and Kivie Moldave, Academic Press, New York (1980).

*Methods in Enzymology*, vol. 68, "Recombinant DNA," edited by Ray Wu, Academic Press, New York (1981).

*Methods in Enzymology*, vol. 100, "Recombinant DNA (Part B)," edited by Ray Wu, Lawrence Grossman and Kivie Moldave, Academic Press, New York (1983).

*Methods in Enzymology*, vol. 101, "Recombinant DNA (Part C)," edited by Ray Wu, Lawrence Grossman and Kivie Moldave, Academic Press, New York (1983).

*Principles of Gene Manipulation, An Introduction to Genetic Engineering*, 2nd Edition, edited by R. W. Old and S. B. Primrose, University of California Press (1981).

H. V. Bernard, et al., Gene (1979) 5, 59.

A. B. Oppenheim, et al., J. Mol. Biol. (1982) 158, 327.

E. Remaut, et al., Gene (1981) 15, 81.

EXAMPLE 1

Expression Vectors

I. p579

The vector p579, shown in FIG. 19 and described in detail under Description of the Figures, is composed of a $P_L$ L promoter, and N utilization site (Nut$_L$), the $C_{II}$ ribosomal binding site bounded by unique EcoRI and NdeI restriction sites, an ATG initiation codon and the $T_1T_2$ transcription termination signals derived from the end of the rrnB ribosomal RNA gene operon of *Escherichia coli*. These elements are cloned on pBR322 carrying the ampicillin resistance gene. Other features are shown in FIG. 19.

p579 was prepared by inserting the $T_1T_2$ transcription termination signals contained on the plasmid pPS1 into the HindIII site of the vector pRO211. pRO211 is shown in FIG. 2. pPS1 has been described in Sarmientos, et al., Cell (1983) 32, 1337-1346 and has been deposited with the American Type Culture Collection under ATCC Number 39807. p579 and its derivatives containing eucaryotic genes may be maintained in suitable *Escherichia coli* hosts. The most important feature of the host is that it provides the thermosensitive repressor cI857 and the antitermination N protein. (Gottesman, M. et al., J. Mol. Biol. (1980) 140, 57-75).

p579 has numerous advantages over previously described expression vectors including:

1. extremely high levels of expressions

This vector is capable of directing expression of foreign proteins in *E. coli* at levels as high as 42% of the total cellular protein. This level of expression is higher than that described for other similar $\lambda P_L$ plasmids lacking the $T_1T_2$ transcription termination sequences.

2. transcription termination signals

The vector p579 contains the $T_1T_2$ transcription termination signals placed "downstream" from the $\lambda P_L$ promoter and $C_{II}$ ribosomal binding site. The high levels of expression which are obtained when using this vector, are due in part to the presence of the $T_1T_2$ transcription terminators at the end of the inserted gene, as the T₁T₂ transcription terminators are capable of terminating transcription of N modified RNA polymerase. Thus the transcription terminators prevent the $\lambda P_L$ controlled transcription of undesired plasmid proteins, thereby enhancing the relative yields of the desired protein.

3. replaceable ribosomal binding sites p579 contains a unique EcoRI site which is located "upstream" of the ribosomal binding site, and a unique NdeI site located at the ATG initiation codon. Thus, the ribosomal binding site is bounded by two unique restriction sites. This enables facile excision of the present ribosomal binding site (the $\lambda C_{II}$ ribosomal binding site) and substitution of virtually any other natural or synthetic ribosomal binding site without altering other features of the plasmid. This greatly facilitates optimal expression of desired polypeptides.

4. thermoinducible regulation of expression

The $\lambda P_L$ promoter is inactive when the $C_I$ repressor is bound to it. The cI857 repressor is thermosensitive, that is, it binds to the promoter at 3° C. but is inactivated at 42° C. Thus, by increasing the temperature of fermentation to 42° C. the host bacteria are induced to produce the desired protein.

The advantages of such a system include the following:

(a) a foreign protein which is toxic to *Escherichia coli* can be produced late in the fermentation process thus avoiding early cell death.

(b) overproduction of a protein may stabilize the protein and prevent proteolytic degradation (Cheng, Y. E., et al., Gene (1981) 14, 121). Thus, "instantaneous" overproduction using a tightly regulated promoter such as $\lambda P_L$ may be preferable to continuous low level production.

5. simplified induction protocol

The plasmids derived from p579 are induced at about 42° C. and maintained at 42° C. throughout the period of protein synthesis. The induction protocol for plasmids derived from pMG100 and pND5 described in copending, coassigned U.S. patent application Ser. No. 514,188 requires a temperature shift to 42° C. followed by an extended period of growth at 38° C. The optimal induction protocol for p579 does not require the cooling step to 38° C. and is thus simplified.

6. high copy number

The $\lambda P_L$ promoter in p579 is found on a plasmid with a copy number higher than that of λ transducing phage vectors which are used in *Escherichia coli*. This increases expression levels.

7. ribosome binding site and initiation codon This expression vector contains a strong procaryotic ribosomal binding site (RBS) as well as a translation initiation codon (ATG). Thus, any eucaryotic gene may be cloned without adding an initiation codon. Furthermore, the efficient RBS increases levels of expression. The ribosome binding site is the $\lambda C_{II}$ ribosomal binding site which we previously cloned into the vector pND5. The sequence of the ribosomal binding site is

TAAGGAAGTACTTACAT
ATTCCTTCATGAATGTA.

One base pair is different from the ribosomal binding site found in wild type λ.

8. convenient restriction site

The expression vector has a unique NdeI restriction site which contains within it, the ATG initiation codon. This permits proper positioning of the desired gene. The unique NdeI site is found immediately after the ribosomal binding site.

9. convenient restriction sites for gene insertion

Located 116 base pairs downstream of the NdeI restriction site are unique restriction sites BglII and SmaI, in that order. These unique restriction sites enable facile insertion of desired genes.

10. nut site

N protein, which is provided by the host, binds to the Nut site on the expression vector and thereby prevents termination of transcription at the $t_{RI}$ site or premature transcription termination within the cloned gene.

Strains

Suitable hosts for the described vectors and plasmids are strains of *Escherichia coli* suitable for transformation, including A1637, A2602, A1563, A1645 (c600 r⁻m⁺gal⁺thr⁻leu⁻lac⁻b1 (λcI857 ΔH1 ΔBamHI N⁺) and A2097 (A1645 lac Δ_χ_A21 proC::Tn 10).

EXAMPLE 2

Animal Growth Hormones

I. pHG44

The construction of pHG44 is shown in FIG. 6, described in the Description of the Figures and deposited under ATCC No. 39806. The plasmid was derived from the pRO12 plasmid shown in FIG. 2 by insertion of the T₁T₂ transcription termination sequences from the plasmid pPS1 which is shown in FIG. 6, described in Sarmientos, et al., Cell (1983) 32, 337–1346 and deposited under ATCC No. 39807. The presence of the T₁T₂ termination sequences prevents long run-on mRNA transcripts, and thus prevents high-level expression of the β-lactamase gene and possibly other undesired proteins under the control of the $\lambda P_L$ promoter.

The plasmid pHG44 has been introduced into *Escherichia coli* strain A2097 by transformation using methods known to those of ordinary skill in the art. This strain produced upon growth and induction an analog of bovine growth hormone (bGH) having the amino acid sequence met-asp-gln added to the amino-terminus of the phenylalanine form of the authentic bGH. The amount of bGH analog produced by pHG44 was about 37–42% of the total protein produced by the bacteria as calculated by scanning Coomasie-stained SDS polyacrylamide gels.

The methods used to grow the strain, recover the bGH analog produced and purify the bGH analog, are described in Example 5. The level of expression is higher than that obtained from PRO12 (Table I) due to a significant reduction in β-lactamase expression effected by the introduction of the T₁T₂ termination sequences at the 3' terminus of the bGH gene.

II. pSAL 5600-1

The construction of pSAL 5600-1 is shown in FIG. 10 and described in the Description of the Figures. The plasmid pSAL 5600-1 was derived from pSAL 5200-6 (shown in FIG. 3) by insertion of the T₁T₂ termination sequences from the plasmid pPS1(ATCC No. 39807).

The plasmid pSAL 5600-1 was introduced into *Escherichia coli* strain A1645 by transformation using methods known to those of ordinary skill in the art. This strain produced upon growth and induction an analog of bGH having the amino acid methionine added to the amino-terminus of the phenylalanine form of natural bGH. The amount of bGH analog produced by pSAL 5600-1 strains was about 22–28% of the total protein produced by the bacteria as calculated by scanning Coomasie-stained SDS polyacrylamide gels. The methods used to grow the strain, recover the bGH analog produced and purify the bGH analog, are the same as those described for pHG44 in Example 5.

The level of expression was higher than that obtained from pSAL 5200-6 strains due to a significant reduction in β-lactamase expression effected by the introduction of the $T_1T_2$ termination sequences at the 3' terminus of the bGH gene.

III. p3009

The construction of p3009 is shown in FIG. 11 and described in the Description of the Figures. The plasmid p3009 was obtained by insertion of the NdeI-NdeI porcine growth hormone cDNA fragment into the unique NdeI site of the p579 expression vector (FIG. 19). The porcine growth hormone (pGH) fragment was isolated from p3008 (ATCC No.39804) by an NdeI digestion.

The plasmid p3009 was introduced into *Escherichia coli* strain A1645 by transformation using methods known to those of ordinary skill in the art. This strain produced upon growth and induction an analog of pGH having the amino acid methionine added to the amino-terminus of the phenylalanine form of the natural pGH. The amount of pGH analog produced was about 30–35% of the total protein produced by the bacteria as calculated by scanning Coomasie-stained SDS polyacrylamide gels. The methods used to grow the strain, recover the pHG analog produced and purify the pGH analog, are the same as those described for pHG44 in Example 5.

The level of expression of p3009 was higher than that obtained from p3008 strains due to a significant reduction in β-lactamase expression effected by the introduction of the $T_1T_2$ termination sequences at the 3' terminus of the pGH gene.

IV. p5003

The construction of p5003 is shown in FIG. 12 and described in the Description of the Figures. p5003 has been deposited with the American Type Culture Collection under ATCC No. 39792. The plasmid was obtained by insertion of the NdeI-NdeI chicken growth hormone cDNA fragment from p5002 into the unique NdeI site of the p579 expression vector.

The plasmid p5003 was introduced into *Escherichia coli* strain A2097 by transformation using methods known to those of ordinary skill in the art. This strain produced upon growth and induction an analog of chicken growth hormone (cGH) having the amino acid methionine added to the aminoterminus of the phenylalanine form of the natural cGH. The amount of cGH analog produced was about 30-35% of the total protein produced by the bacteria as calculated by scanning Coomasie-stained SDS polyacrylamide gels. The methods used to grow the strain recover the cGH analog produced and purify the cGH analog, are the same as those described for pHG44 in Example 5.

The level of expression of p5003 was higher than that obtained from p5002 strains due to a significant reduction in β-lactamase expression effected by the introduction of the $T_1T_2$ termination sequences at the 3' terminus of the cGH gene.

TABLE I[1]

| Plasmid | % bGH[2] | Remarks |
| --- | --- | --- |
| pRec 2/3 | 23 | $Amp^R$ |
| pRO11 | 28 | $Amp^R$ |

TABLE I[1]-continued

| Plasmid | % bGH[2] | Remarks |
| --- | --- | --- |
| pRO12 | 30–36 | $Amp^R$ |
| pHG44 | 37–42 | $Amp^R, T_1T_2$ |
| pHG50 | 37–42 | $Amp^R, T_1T_2; cI^{434}$ |
| pSAL-130/5 | 39–44 | $AmpR; CHCN; T_1T_{22}$ |
| pSAL-170/10 | 40–46 | $Tet^R; CHCN; T_1T_2$ |

1. The table summarizes the bGH expression levels of various plasmids derived from pRO211. The plasmids pRec 2/3 and pRO11 are described in copending, coassigned U.S. Pat. application Ser. No. 514,188, filed July 15, 1983.
2. Amount of bGH produced as percentage of total bacterial protein.

ABBREVIATIONS

CHCN = Constitutive high copy number
$Amp^R$ = Ampicillin resistance
$Tet^R$ = Tetracycline resistance
$T_1T_2$ = Transcription termination sequences
$cI^{434}$ = Plasmid stabilization $cI^{434}$ system

EXAMPLE 3

Human Cu-Zn Superoxide Dismutase (SOD)

I. pSODβ$_1$TT-1

The construction of pSODβ$_1$TT-1 is shown in FIG. 16 and described in the Description of the Figures. The plasmid pSODβ$_1$TT-1 was obtained by insertion of the $T_1T_2$ termination sequences at the 3' end of the SOD gene found in pSODβ$_1T_{11}$ (FIG. 15).

The plasmid pSODβ$_1$TT-1 was introduced into *Escherichia coli* strain A1645 by transformation using methods known to those of ordinary skill in the art. This strain produced upon growth an SOD analog. The amount of SOD analog produced was about 10–15% of the total protein produced by the bacteria as calculated by scanning Coomasie-stained SDS polyacrylamide gels.

The methods used to grow the strain, recover the SOD analog produced and purify the SOD analog, are described in Example 6.

The level of expression of pSODβ$_1$TT-1 was higher than that obtained from pSODβ$_1T_{11}$ (Table II) due to the $T_1T_2$-induced reduction in transcription and translation of non-desired DNA sequences.

The human Cu-Zn SOD analog produced differs from natural human Cu-Zn SOD in that the amino terminus alanine is not acetylated, as demonstrated by amino acid sequencing stoichiometry. The natural human SOD is acetylated at the amino terminus alanine (Hartz, J. W. and Deutsch, H. F., J. Biol. Chem. (1972) 247, 7043-7050, Jabusch, J. R., et al., Biochemistry (1980) 19, 2310-2316; Barra, et al., FEBS Letters (1980) 120, 53 and Oberley, L. W., *Superoxide Dismutase*, Vol. I, CRC Press, Florida, (1982), pp. 32-33). The natural human SOD is glycosylated (Huber, W., U.S. Pat. No. 3,579,495, issued May 18, 1971). Bacterial-produced human SOD is almost certainly not glycosylated as *Escherichia coli* does not glycosylate proteins which it produces. The amino acid sequence of the bacterial-produced SOD analog is identical to that of mature human SOD and does not contain a methionine residue at its N-terminus.

TABLE II

| Plasmid | RBS | % SOD[3] | Remarks |
| --- | --- | --- | --- |
| pSODα2 | $C_{II}$ | 0.1–0.3 | $Amp^R$ |
| pSODβ1 | $BLA^1$ | 3–8 | $Amp^R$ |
| pSODβ$_1T_{11}$ | $BLA^1$ | 8–13 | $Tet^R$ |
| pSODβ$_1$TT-1 | $BLA^1$ | 10–15 | $Tet^R; T_1T_2$ |

TABLE II-continued

| Plasmid | RBS | % SOD[3] | Remarks |
|---|---|---|---|
| pSODβ₁-BA2 | BLA[2] | 2-4 | Amp[R] |

1. Promoter and ribomosal binding site of β-lactamase gene.
2. Synthetic ribosomal binding site corresponding to that of the β-lactamase gene.
3. Amount of SOD analog produced expressed as percentage of total bacterial protein.

ABBREVIATIONS

Amp[R] = Ampicillin resistance
Tet[R] = Tetracycline resistance
T₁T₂ = Transcription termination sequences

EXAMPLE 4

Human Apolipoprotein E3 (Apo-E3)

I. pTV-170

The construction of pTV-170 is shown in FIG. 20 and described in the Description of the Figures. The plasmid PTV-170 was obtained by insertion of the NdeI-NdeI Apo-E3 fragment derived from pApoE-EX2 (ATCC No. 39787) into the unique NdeI site of the expression vector p579.

pTV-170 was introduced into *Escherichia coli* strain A1645 by transformation using methods known to those of ordinary skill in the art. The clone obtained produced upon growth human ApoE3, presumably having the amino acid methionine added to the amino-terminus of natural human ApoE3. The amount of human ApoE3 analog produced was about 1% of the total protein produced by the bacteria as calculated by scanning of Coomasie-stained SDS polyacrylamide gels. The methods used to grow the strain are described in Example 7.

II. pTV-194

The construction of pTV-194 is shown in FIG. 22 and is described in the Description of the Figures. pTV-194 was derived from pTV-170 (FIG. 20) by replacing the C$_{II}$ ribosomal binding site with the β-lactamase promoter and ribosomal binding site derived from pBLA11. pBLA11 contains the promoter and ribosomal binding site of the β-lactamase gene found in pBR322 between coordinates 4157 and 4353. An EcoRI linker was added upstream of the promoter and a multi-restriction site linker was added immediately after the initiation codon ATG. Thus the sequence of the coding strand beginning with the initiation codon is ATGAGCTCTAGAATTC. pBLA11 was deposited in the American Type Collection Center as ATCC No. 39788. pTV-194 was introduced into *Escherichia coli* strain A1645 by transformation using methods known to those of ordinary skill in the art. The clone obtained produced upon growth an analog of human ApoE3, presumably having the amino acid methionine added to the amino-terminus of natural human ApoE3. The amount of human Apo-E analog produced was about 3% of the total protein produced by the bacteria as calculated by scanning Coomasie-stained SDS polyacrylamide gels. The methods used to grow the strain are the same as described for pTV-170 in Example 7.

III. pTV-214

The construction of pTV-214 is shown in FIG. 24 and is described in the Description of the Figures. pTV-214 was derived from pTV-190 (shown in FIG. 21 and described in the Description of the Figures) by insertion of a synthetic DNA fragment coding for the 14 amino acid amino-terminal sequence of human growth hormone into the unique NdeI site of pTV-190.

pTV-214 was introduced into *Escherichia coli* strain A1645 by transformation using methods known to those of ordinary skill in the art. The clone obtained produced upon growth and induction an analog of human ApoE3 having at its amino terminus the 14 amino acid amino-terminal sequence of human growth hormone, followed by methionine, attached to the sequence of mature human ApoE3. The amount of human ApoE analog produced was about 2% of the total protein produced by the bacteria as calculated by scanning Coomasie-stained SDS polyacrylamide gels. The methods used to grow the strain are the same as those described for pTV-170 in Example 7.

EXAMPLE 5

Growth of pHG44

I. Stock Cultures

Stock cultures of pHG44 were grown on casein medium (see Inoculum), then diluted two-fold with freezing medium and stored at −80° C. Freezing medium contains per 500 ml:

| | |
|---|---|
| K₂HPO₄ | 6.3 g |
| KH₂PO₄ | 1.8 g |
| Na Citrate | 0.45 g |
| MgSO₄.7H₂O | 0.09 g |
| (NH₄)₂SO₄ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2–10% inoculum culture and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| K₂HPO₄ | 2.5 g/l |
| MgSO₄.7H₂O | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine, and ampicillin in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| FeCl₃ | 16 g/l |
| ZnCl₂.4H₂O | 2 g/l |
| CoCl₂.6H₂O | 2 g/l |
| Na₂MoO₄.2H₂O | 2 g/l |
| CaCl₂.2H₂O | 1 g/l |
| CuCl₂ | 1 g/l |

| -continued | |
|---|---|
| H$_3$BO$_3$ | 0.5 g/l |
| Conc. HCl | 100 ml/l |

The medium is inoculated with 0.5–10% inoculum culture and incubated at 30° C. Agitation-aeration rates are set to maintain dissolved oxygen level above 20% air saturation. The pH is maintained at 7±0.2 with NH$_3$. Once cell concentration reaches about 3.5 g/l (OD$_{660=10}$) induction is started.

The temperature is raised to 42° C. and maintained at 42° C. for 1–5 hours. The culture is then chilled and cells are recovered by centrifugation for hormone purification.

Recovery of bGH

Thirteen kilograms of bacterial cells (wet cake) are resuspended in 5 volumes of a solution containing 50 mM sodium phosphate buffer (pH 7.4), 50 mM EDTA and 100 mM NaCl, using a Polytron (Kinematica) blender, while controlling the blender's speed to minimize foaming. The homogeneous suspension is continuously passed through a Dynomill cell disruptor KD5 (Willy A. Bachofen, Basel) at a rate of 80 liter per hour and the homogeneous suspension of disrupted cells clarified by centrifugation in a CEPA 101 centrifuge at a flow rate of 45 liter per hour. The precipitate from the centrifugation step was collected and resuspended in 15.5 liters of 50 mM sodium phosphate buffer (pH 7.4) containing 50 mM EDTA. Lysozyme is added to a final concentration of 0.05 mg/ml and the suspension incubated for 16 hours at 37° C. Triton X-100 is added to a final concentration of 1%. The suspension is then incubated for 30 min at room temperature, sonicated in a continuous flow cell sonificator (Heat System) at a rate of 18 liters per hour and centrifuged in a CEPA 101 centrifuge. The precipitate is collected, resuspended in 50 mM sodium phosphate buffer (pH 7.4), sonicated as above, and centrifuged in a CEPA 101 centrifuge. The cells are resuspended in 15.5 liters of 50 mM sodium phosphate buffer (pH 7.4) containing 50 mM EDTA and 100 mM NaCl and twice precipitated and resuspended in 15.5 liters of distilled water. The precipitate is collected by centrifugation and stored at −20° C.

Purification of bGH

The precipitate is resuspended in 30–40 liters distilled water and solubilized by titration with 0.5 N NaOH to pH 11.8. The solution is then continuously sonicated and clarified by centrifugation in CEPA 101 centrifuge if necessary, or filtered through Whatman No. 1 paper.

The clarified protein solution (32.6 liters containing 297,000 OD's at 280 nm) is divided into separate portions (6×5.4 liters) each containing 50,000–60,000 OD's. Each portion is ultrafiltered separately through a Millipore Pellicon ultrafilter equipped with three 100,000 molecular weight cutoff cassettes (type PTHK) of 5 ft$^2$ area each. A 5.4 liter portion is concentrated to 1 liter retentate volume. The ultrafiltrate is collected and saved. The retentate is diluted back to its original volume with fresh 10 mM Borate buffer pH 11.8, and mixed well. The batch is concentrated again to 1 liter retentate volume. The ultrafiltrate is collected and combined with the first ultrafiltrate. When the running total of the OD's in the ultrafiltrates equals 20% of the OD's initially charged to the ultrafilter, the retentate volume on the next concentration step is taken to 0.5 liters instead of 1 liter. The cycle of concentration and dilution with 10 mM Borate buffer is continued until the ultrafiltrate from a retentate volume of 0.5 liters has an absorbance at 280 nm (1-cm cell) of less than 0.1. This normally takes between 9 and 12 cycles of concentration and dilution. The final retentate is discarded.

All ultrafiltrates are combined and adjusted to pH 9.0 with 6N HCl. The other 5.4-liter portions are ultrafiltered in the same fashion, and all pH adjusted ultrafiltrates are combined. A typical run produces a total of 380 liters of ultrafiltrates with an absorbance of 0.26 equivalent to 100,000 OD's and requires 24 to 40 hours to complete.

The combined ultrafiltrates (380 liters containing 100,000 OD's at 280 nm) from the 100K ultrafiltration step are loaded onto a Sepharose CL-6B DEAE ion-exchange column at a linear flow velocity of 23 cm/hr (25 liter/hr). The 37-cm diameter 15-cm high column is washed with two bed volumes (32 L) of 10 mM Borate buffer at pH 9.0. The eluate from the loading and washing steps is discarded. A step change in eluent to 10 mM Borate, 100 mM sodium chloride, pH 9, displaces the bGH off the column. The elution flow velocity is 23 cm/hr. The progress of the run is monitored by following absorbance of the eluate at 280 nm. The bGH peak is collected in 4 to 5 bed volumes (84 liters containing 43,000 OD's at 280 nm) and then concentrated to approximately 10 mg/ml using a Millipore Pellicon ultrafiltration device with a 10,000 molecular weight cutoff cassettes. The solution is then lyophilized. The yield is approximately 70 g of pure bGH.

EXAMPLE 6

Activity of bGH Analog Produced by pHG44

1. Radioimmunoassay Comparison of bGH Analog with Natural bGH

A solution containing 100 ng/ml bGH analog was prepared in phosphate buffered saline (1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural bGH.

2. Radioreceptor Binding Assay

A radioreceptor binding assay was performed with rabbit liver membranes as described by Tushima, T. and Freisen, H. G., (Y. Chin., Endocr..Metab. (1973), 37, 3) using $^{125}$I-bGH as the tracer and authentic bGH solutions for the construction of calibration curves. Samples were incubated in triplicate for two hours at room temperature in 0.3 ml of assay buffer (50 mM Tris, 15 mM CaCl$_2$ and 5 mg/ml bovine serum albumin, pH 7.6). The tubes contained $^{125}$I-bGH (20,000 cpm of preparation of 30–60 μci/μg), 150–250 μg liver membrane protein and either natural bGH (1–100 ng) or extracts of bacterial bGH. The result demonstrates that the bGH activity of the bGH analog is comparable to that of natural bGH.

3. Tibia Test

The bioactivity of the pRO12 produced bGH analog recovered from bacterial cells according to Example 5 was evaluated by a tibia test. (Parlow, A. F., et al., Endocrinology (1965) 77, 1126). Rats were hypophysectomized at 28–30 days of age, then kept for 10–14 days without treatment. Bovine growth hormone derived from bone pituitaries or from recombinant *Escherichia coli* was dissolved in 0.15 M NaCl with 0.01 M borate, pH 10.0. Rate (4–7 per group) received daily subcutaneous injections of bGH solutions (5–125μg/- day in 0.2 cc) for 5 days while kept on a normal diet (Purina Rat-Chow and water adlibitum). The animals were sacrificed on the 6th day, their foreleg knee-bones taken out, cut longitudinally, fixed with acetone and stained with 2% AgNO$_3$. The width of the epiphyseal plates was measured by observation through a dissecting binocular (Nikon). Mean values (40 readings per rat) were used for the construction of long dose-response curves. The results demonstrated that the bGH activity of the pHG44-produced bGH analog is comparable to that of natural bGH.

EXAMPLE 7

Growth of pSOD$\beta_1$TT-1

1. Stock Cultures

Stock cultures of pSOD$\beta_1$T$_{11}$ were grown on casein medium (see Inoculum), then diluted two-fold with freezing medium and stored at −80° C. Freezing medium contains per 500 ml:

|  |  |
|---|---|
| K$_2$HPO$_4$ | 6.3 g |
| KH$_2$PO$_4$ | 1.8 g |
| Na Citrate | 0.45 g |
| MgSO$_4$.7H$_2$O | 0.09 g |
| (NH$_4$)$_2$SO$_4$ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2-10% innoculum and incubated 15 hours at 30° C., pH 7±0.5 with agitation and aeration to maintain a dissolved oxygen level above 20% air saturation.

III. Production

The production medium contains:

|  |  |
|---|---|
| Casein hydrolysate | 20 g/l |
| Yeast extract | 10 g/l |
| K$_2$HPO$_4$ | 2.5 g/l |
| MgSO$_4$.7H$_2$O | 1 g/l |
| NaCl | 5 g/l |
| Biotin | 0.1 mg/l |
| Thiamine | 1 mg/l |
| Trace elements solution | 3 ml/l |
| CuSO$_4$ | 0.8 g/l |
| ZnSO$_4$ | 10 mg/l |

The medium also contains 12.5 mg/liter tetracycline. The tetracycline is optional for production, but is always found in the medium used for growing the inoculum.

Biotin, thiamine and tetracycline in concentrated solution were filter sterilized separately and added to the sterile production medium before inoculation. Sterile glucose solution was added initially to supply 10 g/l. At the induction step another 10 g/l of glucose was added.

The trace elements solution contains:

|  |  |
|---|---|
| FeCl$_3$ | 16 g/l |
| ZnCl$_2$.4H$_2$O | 2 g/l |
| CoCl$_2$.6H$_2$O | 2 g/l |
| Na$_2$MoO$_4$.2H$_2$O | 2 g/l |
| CaCl$_2$.2H$_2$O | 1 g/l |
| CuCl$_2$ | 1 g/l |
| H$_3$BO$_3$ | 0.5 g/l |
| Conc. HCl | 100 ml/l |

The medium is inoculated with 0.5-10% inoculum culture and incubated at 30° C. Agitation-aeration rates are set to maintain a dissolved oxygen level above 20% air saturation. The pH is maintained at 7±0.2 with NH$_3$. Once cell concentration reaches about 3.5 g/l (OD$_{660=10}$) induction is started.

The temperature is raised to 42° C. and maintained at 42° C. for 1-5 hours. The culture is then chilled and cells are recovered by centrifugation for enzyme purification.

Recovery Of SOD

One and half kilograms of bacterial cells (wet cake) are suspended in 12 liters of 50 mM sodium phosphate (pH 7.8), in a Polytron (Kinematica) blender while controlling the speed to minimize foaming. The homogeneous suspension is continuously passed through a Dynomill cell disrupter KD5 (Willy, A. Bachofen, Basel). The homogeneous suspension of disrupted cells is sonicated using a continuous flow cell and centrifuged in a CEPA 101 centrifuge. The supernatant is heated for 2 hours at 65° C., cooled and centrifuged as before. The clear supernatant is concentrated to 1 liter in a Millipore Pellicon ultrafiltration device using 10,000 molecular weight cutoff cassettes (type PTGC). The concentrated protein solution is passed through a DEAE-Sepharose column (2 Kg DEAE Sepharose) equilibrated with 150 mM sodium phosphate buffer (pH 7.8). The flow through solution is collected, concentrated and dialyzed in a Pellicon ultrafiltration device against 20 mM Tris-HCl, pH 7.8, and then applied on to a QAE-Sepharose column equilibrated with 20 mM Tris-HCl buffer. The column is developed with a 20 mM Tris HCl buffer, pH 7.8, and a salt gradient (10–200 mM NaCl). SOD-containing fractions are collected, concentrated using a Pellicon ultrafiltration device, dialzed against distilled water and then brought to 100 mM sodium acetate by adding 1 M sodium acetate buffer, pH 4.8. The protein solution is then further separated on a CM-Sepharose column equilibrated with 100mM sodium acetate buffer, pH 4.7. The column is developed using the same buffer and a salt gradient (100–500mM NaCl). SOD containing fractions are collected, concentrated using a Pellicon ultrafilter device and lyophilized.

EXAMPLE 8

Activity of SOD Produced By pSOD$\beta_1$T$_{11}$

The enzymatic activity of the SOD analog produced by pSOD$\beta_1$T$_{11}$ prepared in Example 7 was assayed by monitoring the inhibition of reduction of ferricytochrome-c as described by McCord and Fridovich, J. Biol. Chem. (1969), 244, 6049–6055. The results demonstrated that the activity of pSOD$\beta_1$T$_{11}$-produced SOD analog was comparable to that of natural human SOD and to that of bovine SOD (Orgotein: Grunenthal GMBH).

EXAMPLE 9

Growth of pTV-170

1. Stock Cultures

Stock cultures of pTV-170 were grown on casein medium (see Inoculum), then diluted two-fold with freezing medium and stored at −80° C. Freezing medium contains per 500 ml:

| | |
|---|---|
| $K_2HPO_4$ | 6.3 g |
| $KH_2PO_4$ | 1.8 g |
| Na Citrate | 0.45 g |
| $MgSO_4.7H_2O$ | 0.09 g |
| $(NH_4)_2SO_4$ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2–10% innoculum and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| $K_2HPO_4$ | 2.5 g/l |
| $MgSO_4.7H_2O$ | 1 g/l |
| NaCl | 5 g/l |
| Biotin | 0.1 mg/l |
| Thiamine | 1 mg/l |
| Trace elements solution | 3 ml/l |

The medium also contained 100 mg/liter ampicillin. The ampicillin is optional for production but is always found in the medium used for growing the inoculum.

Biotin, thiamine and ampicillin in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| $FeCl_3$ | 16 g/l |
| $ZnCl_2.4H_2O$ | 2 g/l |
| $CoCl_2.6H_2O$ | 2 g/l |
| $Na_2MoO_4.2H_2O$ | 2 g/l |
| $CaCl_2.2H_2O$ | 1 g/l |
| $CuCl_2$ | 1 g/l |
| $H_3BO_3$ | 0.5 g/l |
| Conc. HCl | 100 ml/l |

The medium is inoculated with 0.5–10% inoculum culture and incubated at 30° C. Agitation-aeration rates are set to maintain dissolved oxygen level above 20% air saturation. The pH is maintained at 7±0.2 with $NH_3$. Once cell concentration reaches about 3.5 g/l ($OD_{660=10}$) induction is started.

The temperature is raised to 42° C. and maintained at 42° C. for 15 minutes. The culture is then chilled and cells are recovered by centrifugation for protein purification.

What is claimed is:

1. A plasmid for the production of bovine growth hormone or porcine growth hormone or a polypeptide analog thereof having substantially the same amino acid sequence as, and the biological activity, of the bovine or porcine growth hormone which upon introduction into a suitable Escherichia coli host cell containing the thermolabile repressor $C_I$ renders the host cell capable, upon increasing the temperature of the Escherichia coli host cell to a temperature at which the repressor is inactivated, of effecting expression of DNA encoding the growth hormone or polypeptide analog thereof comprising a double-stranded DNA molecule which includes in 5' to 3' order the following:

(a) DNA which contains the promoter and operator $P_LO_L$ from λ bacteriophage;

(b) a single N utilization site for binding antiterminator N protein produced by the Escherichia coli host cell, the side being $Nut_L$:

(c) a DNA sequence containing the mutant $C_{II}$ ribosomal binding site from λ bacteriophage having the sequence

TAAGGAAGTACTTACAT
ATTCCTTCATGAATGTA;

(d) an NdeI restriction enzyme site including an ATG initiation codon;

(e) DNA encoding bovine or porcine growth hormone or the polypeptide analog thereof inserted into the NdeI restriction enzyme site in phase with the ATG initiation codon;

(f) a DNA sequence which contains a $T_1T_2$ rRNA transcription termination sequence located less than 100 base pairs from the DNA encoding or porcine growth hormone;

and which additionally includes a DNA sequence which contains an origin of replication from the bacterial plasmid pBR322 which is capable of autonomous replication in the Escherichia coli host cell and a DNA sequence which contains a gene associated with a selectable or identifiable phenotypic trait which is manifested when the plasmid is present in the Escherichia coli host cell, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs.

2. A plasmid of claim 1, wherein the phenotypic trait is drug resistance.

3. A plasmid of claim 2, wherein the drug resistance is resistance to ampicillin or tetracyline.

4. A plasmid of claim 1 designated pHG44 deposited under ATCC Accession No. 39805.

5. A plasmid of claim 1 designated p7200-22 having the restriction map shown in FIG. 7.

6. A plasmid of claim 1 designated p3009 having the restriction map shown in FIG. 11.

7. A host plasmid system for production of bovine or porcine growth hormone or a polypeptide analog thereof comprising the plasmid of claims 1, 4, 5, or 6 in a suitable Escherichia coli host cell.

8. The host plasmid system of claim 7, wherein the Escherichia coli host cell is A1637, A1645, A2602, A2097 or A1563.

9. A method for producing bovine or porcine growth hormone or a polypeptide analog thereof which comprises growing the host plasmid system of claim 7 or 8 under suitable conditions permitting production of bovine or porcine growth hormone or polypeptide analog thereof and recovering the resulting bovine or porcine growth hormone or polypeptide analog thereof.

* * * * *

UNITED STATES PATENT AND TRADEMARK OFFICE
CERTIFICATE OF CORRECTION

PATENT NO. : 5,126,252
DATED : June 30, 1992
INVENTOR(S) : Amos B. Oppenheim et al.

It is certified that error appears in the above-indentified patent and that said Letters Patent is hereby corrected as shown below:

Title page, beneath INID Code [19], "Oppenhein et al." should read --Oppenheim et al.--.

Title page, following INID Code [54], the title of the invention, given as "EXPRESSIONS VECTORS CONTAINING LAMBDA PL PROMOTER AND $T_1$ $T_2$ RNA TERMINATION SEQUENCE, PLASMIDS CONTAINING THE VECTORS, HOSTS CONTAINING THE PLASMIDS AND RELATED METHODS" should read
--EXPRESSION VECTORS CONTAINING LAMBDA PL PROMOTER AND $T_1$ $T_2$ rRNA TERMINATION SEQUENCE, PLASMIDS CONTAINING THE VECTORS, HOSTS CONTAINING THE PLASMIDS AND RELATED METHODS--

Title page, in the ABSTRACT, line 16, "identificable" should read --identifiable--.

Column 5, lines 50-51, (correction of alignment),
"CCATATGTCCTTGTCCGGCCTGTTTGCCAACGCTGTGCTC-3'
                          3'-GCGACACGAGGCCCGAGTCGTGGACGTGGTCGACG"
should read
--CCATATGTCCTTGTCCGGCCTGTTTGCCAACGCTGTGCTC-3'
                          3'GCGACACGAGGCCCGAGTCGTGGACGTGGTCGACG--.

UNITED STATES PATENT AND TRADEMARK OFFICE
CERTIFICATE OF CORRECTION

PATENT NO. : 5,126,252  
DATED : June 30, 1992  
INVENTOR(S) : Amos B. Oppenheim et al.

Page 2 of 4

It is certified that error appears in the above-indentified patent and that said Letters Patent is hereby corrected as shown below:

Column 6, line 48, "the $T_1$Thd transcription" should read --the $T_1T_2$ transcription--.

Column 6, line 68, "the TetR gene" should read --the $Tet^R$ gene--.

Column 8, line 11, "the TetR gene." should read --the $Tet^R$ gene.--.

Column 8, line 13, "T1T2 transcription" should read --$T_1T_2$ transcription--.

Column 8, line 39, "T1T2 transcription" should read --$T_1T_2$ transcription--.

Column 9, line 7, "PstI site cf" should read --PstI site of--.

Column 10, line 24, "enzyme sites The first" should read --enzyme sites. The first--.

Column 10, line 32, "sequence Preferably," should read --sequence. Preferably,--.

Column 10, line 67, "$r^-m^+gal^+thr^-leu-lac^-$" should read --$r^-m^+gal^+thr^-leu^-lac^-$--.

Column 11, line 3, "$his^-ile-gal^+$" should read --$his^-ile^-gal^+$--.

UNITED STATES PATENT AND TRADEMARK OFFICE
CERTIFICATE OF CORRECTION

PATENT NO. : 5,126,252
DATED : June 30, 1992
INVENTOR(S) : Amos B. Oppenheim et al.

It is certified that error appears in the above-indentified patent and that said Letters Patent is hereby corrected as shown below:

Column 12, line 62, "the 8 -lactamase" should read --the $\beta$-lactamase--.

Column 14, line 34, "a $P_L$ L promoter," should read --a $P_L$ promoter,--.

Column 18, line 7 in Table I,
    "pSAL-130/5    39-44    AmpR;CHCN;$T_1T_{22}$" should read
--pSAL-130/5    39-44    $Amp^R$;CHCN;$T_1T_2$--.

Column 21, line 11, "($OD_{660=10}$)" should read --($OD_{660} = 10$)--.

Column 22, line 51, "CaCl2" should read --$CaCl_2$--.

Column 22, line 67, "Rate" should read --Rats--.

Column 24, line 13, "($OD_{660=10}$)" should read --($OD_{660} = 10$)--.

Column 24, line 20, "sodium phosphate" should read --sodium phosphate buffer--.

Column 24, line 42, "dialzed" should read --dialyzed--.

Column 25, line 58, "($OD_{660=10}$)" should read --($OD_{660} = 10$)--.

In Claim 1, column 26, line 29, "DNA encoding or" should read --DNA encoding bovine or--.

UNITED STATES PATENT AND TRADEMARK OFFICE
CERTIFICATE OF CORRECTION

PATENT NO. : 5,126,252
DATED : June 30, 1992
INVENTOR(S) : Amos B. Oppenheim et al.

It is certified that error appears in the above-indentified patent and that said Letters Patent is hereby corrected as shown below:

In Claim 4, column 26, line 49, "39805" should read --39806--.

Signed and Sealed this

Twelfth Day of September, 1995

Attest:

BRUCE LEHMAN

*Attesting Officer*     *Commissioner of Patents and Trademarks*